US011006911B2

(12) United States Patent
Liu et al.

(10) Patent No.: US 11,006,911 B2
(45) Date of Patent: May 18, 2021

(54) SYSTEM AND METHOD FOR PET IMAGING

(71) Applicant: SHANGHAI UNITED IMAGING HEALTHCARE CO., LTD., Shanghai (CN)

(72) Inventors: Weiping Liu, Shanghai (CN); Xiaoyue Gu, Shanghai (CN); Jianqiao Chen, Shanghai (CN); Hongdi Li, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 520 days.

(21) Appl. No.: 15/697,581

(22) Filed: Sep. 7, 2017

(65) Prior Publication Data

US 2019/0000406 A1 Jan. 3, 2019

Related U.S. Application Data

(63) Continuation of application No. PCT/CN2017/091118, filed on Jun. 30, 2017.

(51) Int. Cl.
*A61B 6/00* (2006.01)
*A61B 6/03* (2006.01)
(Continued)

(52) U.S. Cl.
CPC .......... *A61B 6/4258* (2013.01); *A61B 6/032* (2013.01); *A61B 6/037* (2013.01); *A61B 6/4275* (2013.01);
(Continued)

(58) Field of Classification Search
USPC ............ 250/363.03, 363.04, 363.05, 370.09, 250/370.11
See application file for complete search history.

(56) References Cited

U.S. PATENT DOCUMENTS

| 6,449,331 B1 | 9/2002 | Nutt et al. |
| 2004/0097800 A1 | 5/2004 | Crosetto |

(Continued)

FOREIGN PATENT DOCUMENTS

| CN | 103829962 A | 6/2014 |
| CN | 106880373 A | 6/2017 |

OTHER PUBLICATIONS

The Extended European Search Report in Europen Application No. 17382275.5 dated May 29, 2019, 9 pages.
(Continued)

*Primary Examiner* — David P Porta
*Assistant Examiner* — Carolyn Fin
(74) *Attorney, Agent, or Firm* — Metis IP LLC

(57) ABSTRACT

The present disclosure relates to a system for imaging. The system may include a supporting assembly and a detector assembly. The supporting assembly may include a detection region to accommodate a subject. The detector assembly may surround the detection region. The detector assembly may be configured to detect radiation rays emitted from the subject located within the detection region. The detector assembly may include a plurality of detector rings. Each detector ring may include a scintillator array and a plurality of photosensors. The plurality of detector rings may be arranged on the supporting assembly in an axial direction of the supporting assembly to form an axial field of view (FOV) having a length no less than 0.75 meters.

20 Claims, 17 Drawing Sheets

(51) Int. Cl.
*G01T 1/20* (2006.01)
*G01T 1/29* (2006.01)

(52) U.S. Cl.
CPC .......... *A61B 6/4411* (2013.01); *A61B 6/4417* (2013.01); *G01T 1/2018* (2013.01); *G01T 1/2985* (2013.01); *A61B 6/4266* (2013.01)

(56) References Cited

U.S. PATENT DOCUMENTS

| | | | |
|---|---|---|---|
| 2004/0195512 A1 | 10/2004 | Crosetto | |
| 2009/0236532 A1* | 9/2009 | Frach | G01T 1/1611 250/363.04 |
| 2012/0001077 A1 | 1/2012 | Inoue et al. | |
| 2012/0320083 A1 | 12/2012 | Zhu et al. | |
| 2013/0303898 A1 | 11/2013 | Kinahan et al. | |
| 2014/0361181 A1* | 12/2014 | Liu | G01T 1/1618 250/366 |
| 2015/0057535 A1 | 2/2015 | Sitek | |
| 2016/0113598 A1* | 4/2016 | Dong | G01G 19/445 600/407 |
| 2016/0321808 A1 | 11/2016 | Zhou et al. | |
| 2017/0176607 A1 | 6/2017 | Liu et al. | |
| 2018/0184992 A1 | 7/2018 | Li et al. | |

OTHER PUBLICATIONS

Hunter W C J el al., Parametric Design Study of a Long Axial Field-of-view PET Scanner Using a Block-Detector Tomograph Simulation of a Cylindrical Phantom, IEEE Nuclear Science Symposium Conference Record, 3900-3903, 2009.
S Surti et al., Impact of Detector Design on Imaging Performance of a Long Axial Field-of-view, Whole-body PET scanner, Physics in Medicine and Biology, 60(13):5343-5358, 2015.
Jean-Marc Vrigneaud et al., Principles and Practice of PET/CT Part1 A Technologist's Guide, Chapter 2, 16-22, 2011.
Giovanni Borasi et al., PET systems: the value of added length, European Journal of Nuclear Medicine and Molecular Imaging, 37(9): 1629-1632, 2010.
William C J Hunter et al., Parametric Design Study of a Long Axial Field-of-View PET Scanner using a Block-Detector Tomograph Simulation of a Cylindrical Phantom, 2009 IEEE Nuclear Symposium Conference Record, 2009, 13 pages.
First Office Action in Chinese Application No. 201710883073.3 dated Oct. 8, 2019, 18 pages.
Search Opinion in International Application No. PCT/CN2017/091118 dated Mar. 29, 2018, 4 pages.
Written Opinion in International Application No. PCT/CN2017/091118 dated Mar. 29, 2018, 4 pages.

* cited by examiner

SYSTEM AND METHOD FOR PET IMAGING

CROSS-REFERENCE TO RELATED APPLICATIONS

This present application is a continuation of International Application No. PCT/CN2017/091118, filed on Jun. 30, 2017, the contents of which are hereby incorporated by reference.

TECHNICAL FIELD

The present disclosure generally relates to medical imaging technology, and more particularly, a system and method for PET imaging.

BACKGROUND

Generally, positron emission tomography (PET) detector units have been set in various medical devices such as, positron emission tomography devices, positron emission tomography-computed tomography (PET-CT) devices, and positron emission tomography-magnetic resonance imaging devices (PET-MRI), in which PET technologies are applied. PET detector units are used to receive radiation rays (e.g., γ rays) generated from a patient's body indirectly by tracer molecules and to provide information relating to the locations of the tracer molecules, which in turn provides functional information of the patient. PET detector units may generate electrical signals based on the radiation rays, and then the electrical signals may be detected and used to reconstruct an image.

A PET detector assembly of a PET imaging system may include a plurality of detector units arranged in a substantially cylindrical configuration. Generally speaking, the more detector units the PET detector assembly includes, the more radiation rays the PET detector assembly may receive, and the higher the sensitivity of a PET imaging system may be. In some embodiments, it may be desirable to perform a whole-body scanning using a PET imaging system. A large axial field-of-view (AFOV) detector assembly may image a large fraction of an object (e.g., the whole body of a patient) in one scan, the sensitivity may be increased, and the scanning time may be shortened. Besides, a large AFOV may facilitate a whole-body dynamic scan that may have the benefits of a low radiation dose, a fast speed, etc. It may be desirable to develop a PET imaging system having a detector assembly with a large AFOV.

SUMMARY

One aspect of the present disclosure relates to a first system for imaging. The first system may include a supporting assembly and a detector assembly. The supporting assembly may include a detection region to accommodate a subject. The detector assembly may surround the detection region. The detector assembly may be configured to detect radiation rays emitted from the subject located within the detection region. The detector assembly may include a plurality of detector rings. Each detector ring may include a scintillator array and a plurality of photosensors. The plurality of detector rings may be arranged on the supporting assembly in an axial direction of the supporting assembly to form an axial field of view (FOV) having a length no less than 0.75 meters.

Another aspect of the present disclosure relates to a second system for PET-CT imaging. The second system may include a supporting assembly, an X ray emission device, a first detector assembly and a second detector assembly. The supporting assembly may include a detection region to accommodate a subject. The detection region may include a first portion and a second portion. The first detector assembly may surround the first portion of the detection region. The first detector assembly may be configured to detect at least a portion of an X ray beam emitted by the X ray emission device and traversing the subject located within the first portion of the detection region. The second detector assembly may surround the second portion of the detection region. The second detector assembly may be configured to detect radiation rays emitted from the subject located within the second portion of the detection region. The second detector assembly may include a plurality of detector rings. Each detector ring may include a scintillator array and a plurality of photosensors. The plurality of detector rings may be arranged on the supporting assembly in an axial direction of the supporting assembly to form an axial field of view (FOV) having a length no less than 0.75 meters.

In some embodiments, the detector assembly may include N detector modules, each of which may include a portion of the plurality of detector rings. The supporting assembly may include N supporting modules. The N detector modules and the N supporting modules may be configured as N imaging units, each of which may include at least one detector module of the N detector modules and at least one supporting module of the N supporting modules.

In some embodiments, at least one of the N imaging units may be detachable.

In some embodiments, the supporting assembly may further include a supporting rail along the axial direction to guide the N imaging units to be assembled.

In some embodiments, the first system may further include a position adjustment assembly configured to align the N imaging units in the axial direction.

In some embodiments, each imaging unit of the N imaging units may have a center. A deviation of the center of a first imaging unit and the center of a second imaging unit may be less than or equal to 1 millimeter.

In some embodiments, (N−2) imaging units of the N imaging units may be located between the first imaging unit and the second imaging unit.

In some embodiments, a deviation of the center of a first imaging unit and the center of a second imaging unit that is located adjacent to the first imaging unit may be less than or equal to 0.2 millimeters.

In some embodiments, a deviation of the center of a first imaging unit and the center of a second imaging unit that is located adjacent to the first imaging unit may be less than or equal to 0.5 millimeters.

In some embodiments, a deviation of the center of a first imaging unit and the center of a second imaging unit that is located adjacent to the first imaging unit may be less than or equal to 0.2 millimeters.

In some embodiments, the length of an axial FOV of an imaging unit of the N imaging units may range from 0.16 meters to 0.3 meters.

In some embodiments, the length of an axial FOV of an imaging unit of the N imaging units may range from 0.1 meters to 0.5 meters.

In some embodiments, a first imaging unit of the N imaging units may have a first transverse diameter, a second imaging unit of the N imaging units may have a second transverse diameter, and the first transverse diameter may be different from the second transverse diameter.

In some embodiments, an axial angle of acceptance may be equal to or larger than an intersection angle of a line of response (LOR) and a transverse plane of the detector assembly, wherein the line of response (LOR) may connect a first scintillator in a third imaging unit and a second scintillator in a fourth imaging unit adjacent to the third imaging unit, and the first scintillator and the second scintillator may detect a coincidence event in a scan of the subject using the first system.

In some embodiments, N may be an integer larger than 1.

In some embodiments, N may be equal to 8.

In some embodiments, N may be between 2 and 20.

In some embodiments, two of the N imaging units may have a first gap in the axial direction less than a width of one scintillator of the scintillator array in the axial direction.

In some embodiments, the first system may further include a cooling assembly configured to cool the detector assembly.

In some embodiments, the cooling assembly may include a cooling medium, a cooling medium generation device, and a distributor, wherein the distributor may be configured to transmit the cooling medium into different portions of the detector assembly.

In some embodiments, the cooling medium may be water or air.

In some embodiments, two adjacent detector rings of the plurality of detector rings may be spaced by a second gap less than 20 millimeters.

In some embodiments, the first gap may be less than 10 millimeters.

In some embodiments, the length of the axial FOV may be larger than or equal to 1 meter.

In some embodiments, the length of the axial FOV may be larger than or equal to 1.5 meters.

In some embodiments, the length of the axial FOV may be larger than or equal to 2 meters.

In some embodiments, the first system and/or the second system may have a spatial resolution higher than or equal to 2.8 millimeters.

In some embodiments, the first system and/or the second system may have a sensitivity higher than or equal to 300 cps/kBq.

In some embodiments, the detection assembly may detect radiation from the subject at a radiation dose less than or equal to 5 mSv in a scan of the subject using the first system.

In some embodiments, the second detector assembly may include N detector modules, each of which may include a portion of the plurality of detector rings. The supporting assembly may include N supporting modules. The N detector modules and the N supporting modules may be configured as N PET units, each of which may include at least one detector module of the N detector modules and at least one supporting module of the N supporting modules.

In some embodiments, at least one of the N PET units may be detachable.

In some embodiments, the supporting assembly may further include a supporting rail along the axial direction to guide the N PET units to be assembled.

In some embodiments, the second system may further include a position adjustment assembly configured to align the N PET units and the first detector assembly in the axial direction.

In some embodiments, each PET unit of the N PET units may have a center. A deviation of the center of a first PET unit and the center of a second PET unit may be less than or equal to 1 millimeter.

In some embodiments, (N−2) PET units of the N PET units may be located between the first PET unit and the second PET unit.

In some embodiments, a deviation of the center of a first PET unit and the center of a second PET unit that is located adjacent to the first PET unit may be less than or equal to 0.2 millimeters.

In some embodiments, a deviation of the center of a first PET unit and the center of a second PET unit that is located adjacent to the first PET unit may be less than or equal to 0.5 millimeters.

In some embodiments, the length of an axial FOV of a PET unit of the N PET units may range from 0.1 meters to 0.5 meters.

In some embodiments, a first PET unit of the N PET units may have a first transverse diameter, a second PET unit of the N PET units may have a second transverse diameter, and the first transverse diameter may be different from the second transverse diameter.

In some embodiments, an axial angle of acceptance may be equal to or larger than an intersection angle of a line of response (LOR) and a transverse plane of the second detector assembly, wherein the line of response (LOR) may connect a first scintillator in a third PET unit and a second scintillator in a fourth PET unit adjacent to the third PET unit, and the first scintillator and the second scintillator may detect a coincidence event in a scan of the subject using the system.

In some embodiments, the supporting assembly may further include a supporting rail along the axial direction to guide the N PET units and the first detector assembly to be assembled.

In some embodiments, two of the N PET units may have a first gap in the axial direction less than a width of one scintillator of the scintillator array in the axial direction.

In some embodiments, the second system may further include a cooling assembly configured to cool the first detector assembly and the second detector assembly.

In some embodiments, the cooling assembly may include a cooling medium, a cooling medium generation device, and a distributor, wherein the distributor may be configured to transmit the cooling medium into different portions of the first detector assembly and the second detector assembly.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
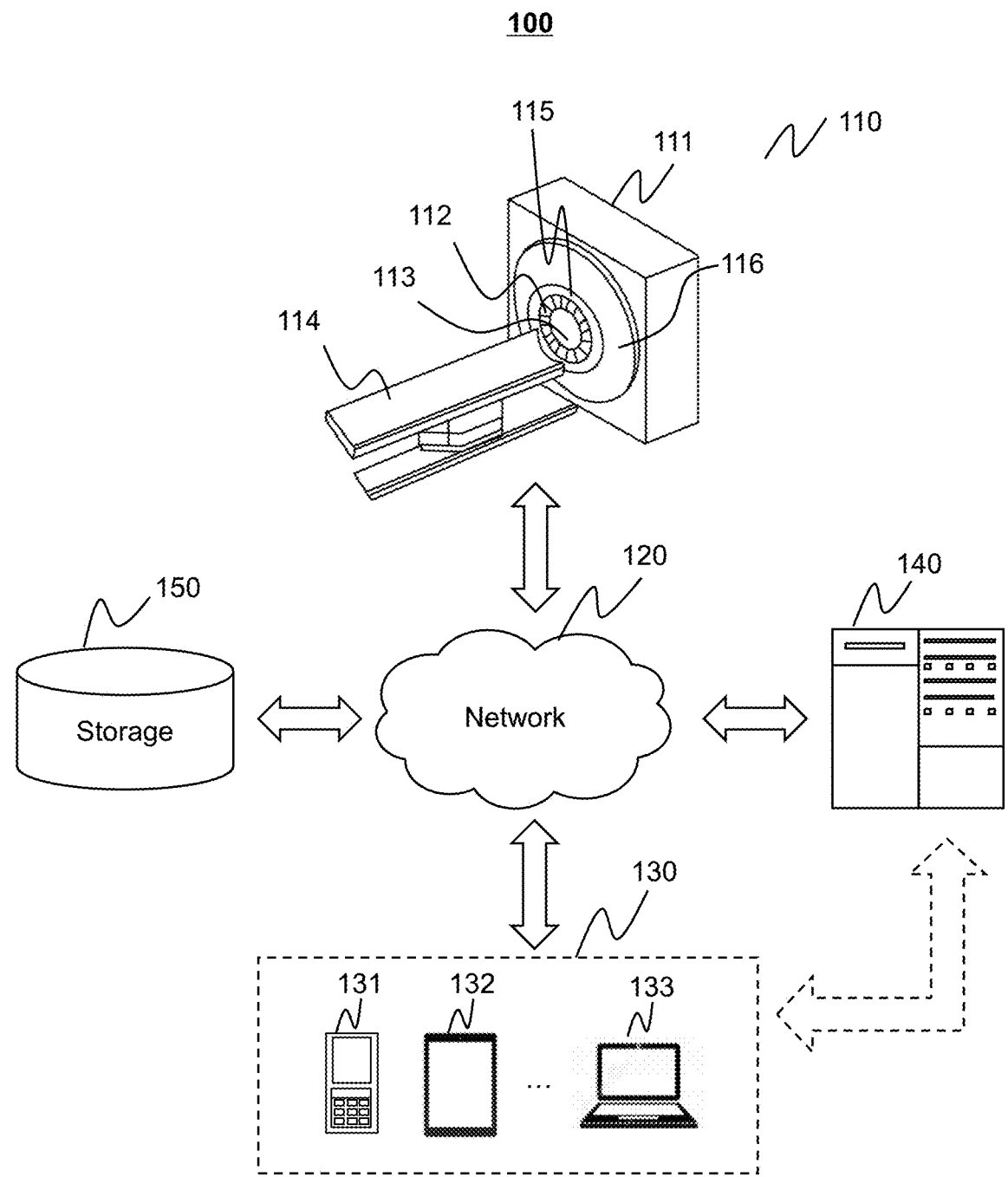
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding a PET imaging system. It is understood that this is not intended to limit the scope of the present disclosure. For persons having ordinary skills in the art, a certain amount of variations, changes and/or modifications may be deducted under guidance of the present disclosure. Those variations, changes and/or modifications do not depart from the scope of the present disclosure.

FIG. 1 is a schematic diagram illustrating an exemplary imaging system 100 according to some embodiments of the present disclosure. As shown, the imaging system 100 may include a scanner 110, a network 120, one or more terminals 130, a processing engine 140, and a storage 150. In some embodiments, the scanner 110, the processing engine 140, the storage 150, and/or the terminal(s) 130 may be connected to and/or communicate with each other via a wireless connection (e.g., the network 120), a wired connection, or a combination thereof. The connection between the components in the imaging system 100 may be variable. Merely by way of example, the scanner 110 may be connected to the processing engine 140 through the network 120, as illustrated in FIG. 1. As another example, the scanner 110 may be connected to the processing engine 140 directly. As a further example, the storage 150 may be connected to the processing engine 140 through the network 120, as illustrated in FIG. 1, or connected to the processing engine 140 directly.

The scanner 110 may scan an object, and/or generate a plurality of data relating to the object. In some embodiments, the scanner 110 may be a medical imaging device, for example, a PET device, a PET-CT device, a PET-MRI device, etc. The scanner 110 may include a supporting assembly 111 (e.g., a gantry), a detector assembly 112, a detection region 113, a table 114, an electronics module 115, and a cooling assembly 116. A subject may be placed on the table 114 for scanning. In the present disclosure, "object" and "subject" are used interchangeably. The detector assembly 112 may detect radiation events (e.g., gamma photons) emitted from the detection region 113. In some embodiments, the detector assembly 112 may include one or more detectors. The detectors may be implemented in any suitable manner, for example, a ring, an arc, a rectangle, an array, or the like, or any combination thereof. See, for example, FIGS. 5A-5D and the description thereof. In some embodiments, a detector may include one or more crystal elements and/or one or more photomultipliers (e.g., silicon photomultiplier (SiPM), photomultiplier tube (PMT)). See, for example, FIGS. 4A-4C and the description thereof. The table 114 may position a subject in the detection region 113. The electronics module 115 may collect electrical signals generated based on the radiation events detected by the detector assembly 112. The cooling assembly 116 may cool the detector assembly 112. More descriptions of the supporting assembly 111, the detector assembly 112, the table 114, the electronics module 115, and the cooling assembly 116 may be found elsewhere in the present disclosure. See, for example, FIG. 2 and the description thereof.

The network 120 may include any suitable network that can facilitate exchange of information and/or data for the imaging system 100. In some embodiments, one or more components of the imaging system 100 (e.g., the scanner 110, the terminal 130, the processing engine 140, the storage 150, etc.) may communicate information and/or data with one or more other components of the imaging system 100 via the network 120. For example, the processing engine 140 may obtain image data from the scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the scanner 110, the terminal(s) 130, and/or the storage 150. For example, the processing engine 140 may process image data and reconstruct an image based on the image data. In some embodiments, the processing engine 140 may be a single server or a server group. The server group may be centralized or distributed. In some embodiments, the processing engine 140 may be local or remote. For example, the processing engine 140 may access information and/or data stored in the scanner 110, the terminal(s) 130, and/or the storage 150 via the network 120. As another example, the processing engine 140 may be directly connected to the scanner 110, the terminal(s) 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device. In some embodiments, the processing engine 140, or a portion of the processing engine 140 may be integrated into the scanner 110.

In some embodiments, a computing device may include a processor, a storage, an input/output (I/O), and a communication port. The processor may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. In some embodiments, the processor may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The storage may store data/information obtained from the scanner 110, the terminal(s) 130, the storage 150, and/or any other component of the imaging system 100. In some embodiments, the storage may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage may store one or more programs and/or instructions to perform exemplary methods described in the present disclosure.

The I/O may input and/or output signals, data, information, etc. In some embodiments, the I/O may enable a user interaction with the processing engine 140. In some embodiments, the I/O may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port may be connected to a network (e.g., the network 120) to facilitate data communications. The communication port may establish connections between the processing engine 140 and the scanner 110, the terminal(s) 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port may be and/or include a standardized communication port, such as RS232, RS485, etc. In some embodiments, the communication port may be a specially designed communication port. For example, the communication port may be designed in accordance with the digital imaging and communications in medicine (DICOM) protocol.

The storage 150 may store data, instructions, and/or any other information. In some embodiments, the storage 150 may store data obtained from the terminal(s) 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing engine 140, the terminal(s) 130, etc.). One or more components in the imaging system 100 may access the data or instructions stored in the storage 150 via the network 120. In some embodiments, the storage 150 may be directly connected to or communicate with one or more other components in the imaging system 100 (e.g., the processing engine 140, the terminal(s) 130, etc.). In some embodiments, the storage 150 may be part of the processing engine 140.

Figure 2:
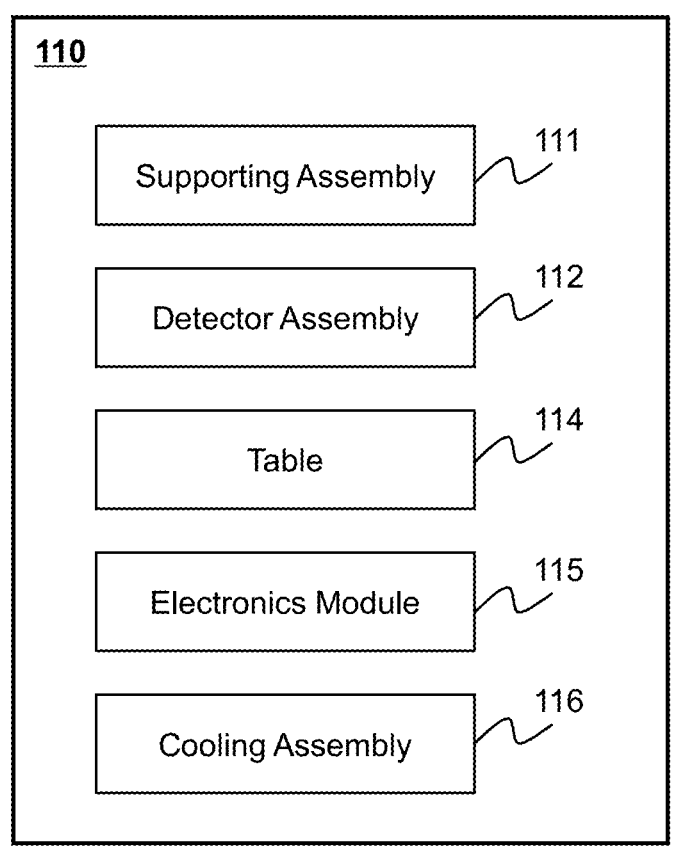
FIG. 2 is a schematic diagram illustrating an exemplary scanner according to some embodiments of the present disclosure.

FIG. 2 is a schematic diagram illustrating an exemplary scanner 110 according to some embodiments of the present disclosure. As illustrated in FIG. 2, the scanner 110 may include a supporting assembly 111, a detector assembly 112, a table 114, an electronic module 115, and a cooling assembly 116.

The supporting assembly 111 may support one or more parts of the scanner 110, for example, the detector assembly 112, electronic module 115, the cooling assembly 116, etc. In some embodiments, the supporting assembly 111 may include a main gantry, a gantry base, a front cover plate, and a back cover plate (not shown). The front cover plate may be connected with the gantry base. The front cover plate may be substantially perpendicular to the gantry base. The main gantry may be mounted on a side face of the front cover plate. The main gantry may include one or more supporting frames to contain the detector assembly 112 and/or the electronic module 115. The main gantry may include a substantially circular opening (e.g., the detection region 113) to accommodate a scanned object. In some embodiments, the opening of the main gantry may be of another shape including, for example, an oval. The term "subject" and the term "object" are used interchangeably in the present disclosure, unless stated otherwise. The back cover plate may be mounted on a side face of the main gantry opposite to the front cover plate. The gantry base may support the front cover plate, the main gantry, and/or the back cover plate. In some embodiments, the scanner 110 may include a shell (e.g., a shell 302 illustrated in FIG. 3) to cover and protect the main gantry.

The detector assembly 112 may detect radiation events (e.g., gamma photons) emitted from the detection region 113. In some embodiments, the detector assembly 112 may receive radiation rays (e.g., gamma rays) and generate electrical signals. The detector assembly 112 may include one or more detector units. One or more detector units may be packaged to form a detector block. More descriptions of the detector block may be found elsewhere in the present disclosure. See, for example, FIGS. 4A-4C and the description thereof. One or more detector blocks may be packaged to form a detector cassette. One or more detector cassettes may be arranged to form a detector ring. One or more detector rings may be arranged to form a detector module. More descriptions of the detector ring may be found elsewhere in the present disclosure. See, for example, FIGS. 5A-5D and the description thereof.

The table 114 may support an object and position the object at a desired position in the detection region 113. In some embodiments, the object may lay on the table 114. The table 114 may be moved under the control of the control module 1004 and reach a desired position in the detection region 113. In some embodiments, the scanner 110 may have a relatively long axial field-of-view (AFOV) (see FIG. 7B), for example, 2-meter long AFOV, and correspondingly, the table 114 may be moved in a wide range (e.g., >2 meters) along the axial direction.

The electronics module 115 may collect and/or process the electrical signals generated by the detector assembly 112. The electronics module 115 may include an adder, a multiplier, a subtracter, an amplifier, a drive circuit, a differential circuit, a integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof. The electronics module 115 may convert an analog signal relating to an energy of radication rays received by the detector assembly 112 to a digital signal. The electronics module 115 may compare a plurality of digital signals, analyze the plurality of digital signals, and determine an interaction position and/or an interaction time of the received radication rays in the detector assembly 112. The electronics module 115 may determine one or more coincidence events based on the plurality of digital signals. The electronics module 115 may determine image data based on the coincidence events and the energies of radiation rays recognized as the coincidence events. In some embodiments, if the detector assembly 112 has a large axial FOV (e.g., 0.75 meters to 2 meters), the electronics module 115 may have a high data input rate from multiple detector channels. For example, the electronics module 115 may handle up to tens of billion events (e.g., coincidence events, single events, etc.) per second. In some embodiments, the data input rate may relate to the number of detector units in the detector assembly 112.

The cooling assembly 116 may produce, transfer, deliver, channel, or circulate a cooling medium to the scanner 110 to absorb heat produced by the scanner 110 during an imaging procedure. In some embodiments, the cooling assembly 116 may be entirely integrated into the scanner 110 and become a part of the scanner 110. In some embodiments, the cooling assembly 116 may be partially integrated into the scanner 110 and associated with the scanner 110. The cooling assembly 116 may allow the scanner 110 to maintain a suitable and stable working temperature (e.g., 25° C., 30° C., 35° C., etc.). In some embodiments, the cooling assembly 116 may control the temperature of one or more target components of the scanner 110. The target components may include the detector assembly 112, the electronics module 115, and/or any other component that generates heat in operation. The cooling medium may be gaseous, liquid (e.g., water), or the like, or any combination thereof. In some embodiments, the gaseous cooling medium may be air. More descriptions of the cooling assembly 116 may be found elsewhere in the present disclosure. See, for example, FIGS. 8A-9B and the description thereof.

Figure 3:
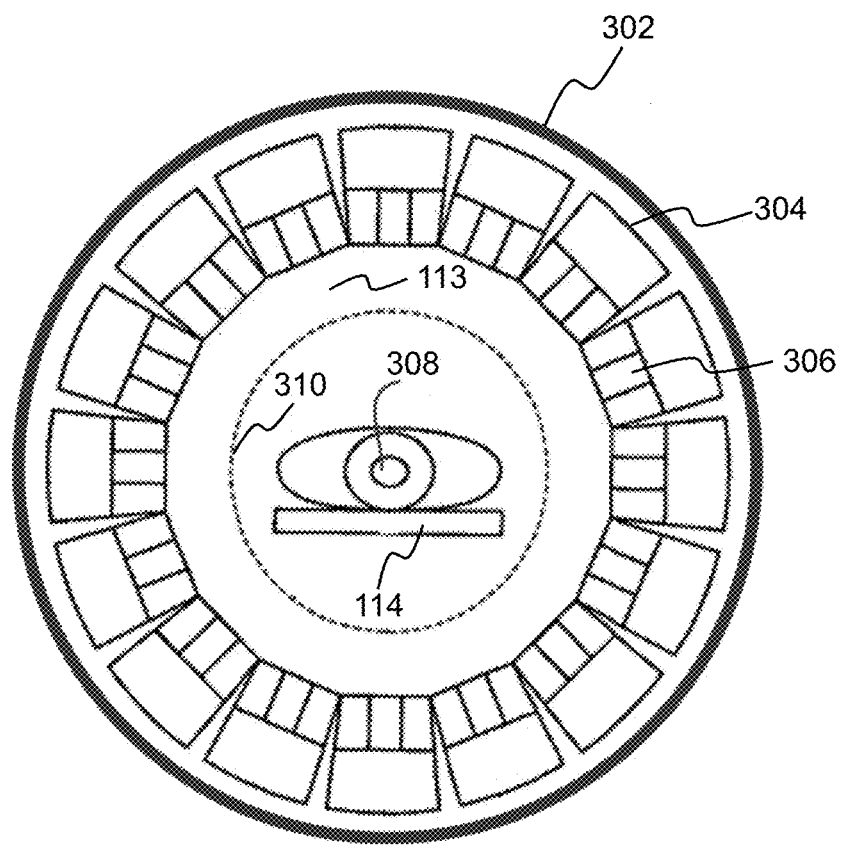
FIG. 3 is a schematic diagram illustrating a side view of an exemplary scanner.

FIG. 3 is a schematic diagram illustrating a side view of an exemplary scanner 110. As illustrated in FIG. 3, a plurality of detector cassettes 304 may be arranged in substantially a ring configuration (also referred to as a detector ring) in the transverse plane. A detector cassette 304 may include one or more detector blocks 306. An exemplary detector block 306 may be found in FIGS. 4A-4C. The detector cassettes 304 may be covered and protected by a shell 302. In some embodiments, the shell 302 may be a hollow cylinder. The region encircled by the detector cassettes 304 may be the detection region 113. The detection region 113 may accommodate a subject 308 to be scanned. The subject 308 may be supported on the table 114. In some embodiments, if the subject 308 is positioned within the range of a transverse FOV, radiation rays emitted from the subject 308 may be detected by the detector cassettes 304. More descriptions of the transverse FOV may be found elsewhere in the present disclosure. See, for example, FIG. 7A and the description thereof.

Figure 4A:
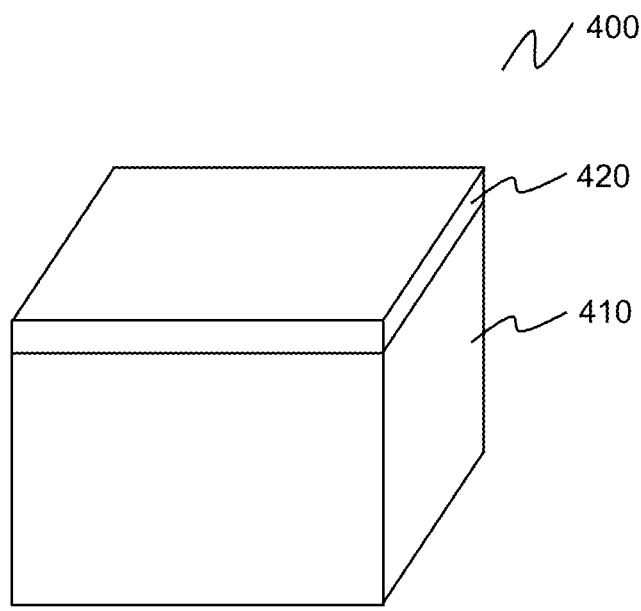
FIGS. 4A-4C are schematic diagrams illustrating an exemplary detector block according to some embodiments of the present disclosure.
Figure 4B:
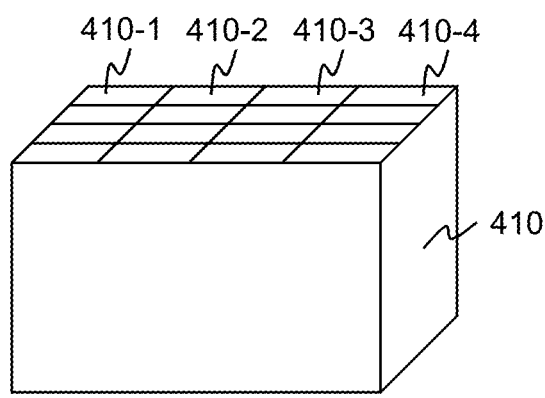
Figure 4C:
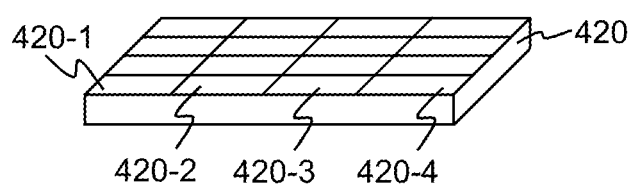

FIGS. 4A-4C are schematic diagrams illustrating an exemplary detector block 306 according to some embodiments of the present disclosure. A detector block 306 may include one or more crystal elements (e.g., the scintillator crystal array 410) and one or more photosensor arrays 420.

As shown in FIG. 4A, the crystal elements may be configured as a scintillator crystal array 410 (also referred to as scintillator array 410). The scintillator array 410 may include one or more scintillators (e.g., the scintillator 410-1, the scintillator 410-2, the scintillator 410-3, the scintillator 410-4, etc. as illustrated in FIG. 4B). A scintillator may scintillate when a radiation ray (e.g., γ ray) photon impinges on the scintillator. The scintillator may absorb the energy of the radiation ray (e.g., γ ray) photon, and convert the absorbed energy into light. In some embodiments, the scintillators of the scintillator array 410 may be arranged in N rows and M columns. N may be an integer larger than 0. M may be an integer larger than 0. In some embodiments, N may be equal to M. In some embodiments, N may be different from M. In some embodiments, the N×M scintillator array may be obtained by making partial cuts through a crystal with a saw. In some embodiments, the cuts may be made to various depths. In some embodiments, the deepest cut may be at the edge of the detector block 306. In some embodiments, two adjacent scintillators of the scintillator array 410 may be filled with a barrier material (e.g., a light-reflective film, etc.). The scintillator may use one or more types of crystals including, for example, NaI(TI), BGO, LSO, YSO, GSO, LYSO, LaBr$_3$, LFS, LuAP, LuI$_3$, BaF$_2$, CeF, CsI(TI), CsI(Na), CaF$_2$(Eu), CdWO$_4$, YAP, or the like, or any combination thereof. Exemplary physical properties of some scintillators may be found in Table 1.

FIG. 4B illustrates an exemplary 4×4 scintillator array. The scintillator array 410 may have a first surface and a second surface opposite to the first surface. The first surface may be a common face of one end of the scintillators (e.g., a top surface) in the scintillator array 410. The second surface may be a common face of the other end of the scintillators (e.g., a bottom surface) in the scintillator array 410. In some embodiments, the first surface or the second surface may face the detection region 113.

A photosensor array 420 may include one or more photosensors (e.g., the photosensor 420-1, the photosensor 420-2, the photosensor 420-3, the photosensor 420-4, etc. as illustrated in FIG. 4C). A photosensor may convert a light signal (e.g., the light output from a scintillator) to an electrical signal. In some embodiments, a photosensor may be a photomultiplier tube (PMT), a silicon photomultiplier (SiPM), etc. In some embodiments, a photosensor (e.g., PMT, or SiPM) may be a single-channel photosensor or a multi-channel photosensor. The photosensor array 420 may be coupled to the scintillator array 410. In some embodiments, the photosensor array 420 may be arranged on the first surface or the second surface of the scintillator array 410. In some embodiments, two photosensor arrays may be arranged on the first surface and the second surface of the scintillator array 410, respectively. In some embodiments, the photosensors of the photosensor array 420 may be arranged in N' rows and M' columns. N' may be an integer larger than 0 but no larger than N. M' may be an integer larger than 0 but no larger than M. In some embodiments, a photosensor may be coupled to one or more scintillators of the scintillator array 410 simultaneously.

TABLE 1

Exemplary physical properties of scintillators in PET (the energy resolution and attenuation coefficients are measured at 511 keV)

| Property | NaI (Tl) | BGO | LSO | YSO | GSO | BaF$_2$ |
|---|---|---|---|---|---|---|
| Density (g/cm3) | 3.67 | 7.13 | 7.4 | 4.53 | 6.71 | 4.89 |
| Effective Z | 50.6 | 74.2 | 65.5 | 34.2 | 58.6 | 52.2 |
| Attenuation length | 2.88 | 1.05 | 1.16 | 2.58 | 1.43 | 2.2 |
| Decay constant (ns) | 230 | 300 | 40 | 70 | 60 | 0.6 |
| Light output (photons/keV) | 38 | 6 | 29 | 46 | 10 | 2 |
| Relative light output | 100% | 15% | 75% | 118% | 25% | 5% |
| Wavelength λ (nm) | 410 | 480 | 420 | 420 | 440 | 220 |
| Intrinsic ΔE/E (%) | 5.8 | 3.1 | 9.1 | 7.5 | 4.6 | 4.3 |
| ΔE/E (%) | 6.6 | 10.2 | 10 | 12.5 | 8.5 | 11.4 |
| Index of refraction | 1.85 | 2.15 | 1.82 | 1.8 | 1.91 | 1.56 |
| Hygroscopic? | Yes | No | No | No | No | No |
| Rugged? | No | Yes | Yes | Yes | No | Yes |
| μ (cm$^{-1}$) | 0.3411 | 0.9496 | 0.8658 | 0.3875 | 0.6978 | 0.4545 |
| μ/ρ (cm$^2$/gm) | 0.0948 | 0.1332 | 0.117 | 0853 | 0.104 | 0.0929 |

It should be noted that the above description of the detector block 306 is merely provided for the purpose of illustration, and not intended to limit the scope of the present disclosure. For persons having ordinary skills in the art, multiple variations and modifications may be made to the detector module 200 under the teachings of the present disclosure. However, those variations and modifications do not depart from the scope of the present disclosure. For example, one or more light guides may be configured between the scintillator array 410 and the photosensor array 420.

Figure 5A:
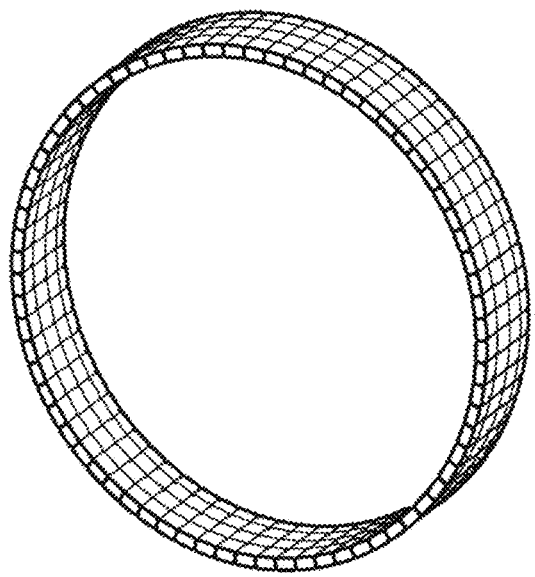
FIGS. 5A-5D are schematic diagrams illustrating exemplary detector rings according to some embodiments of the present disclosure.
Figure 5B:
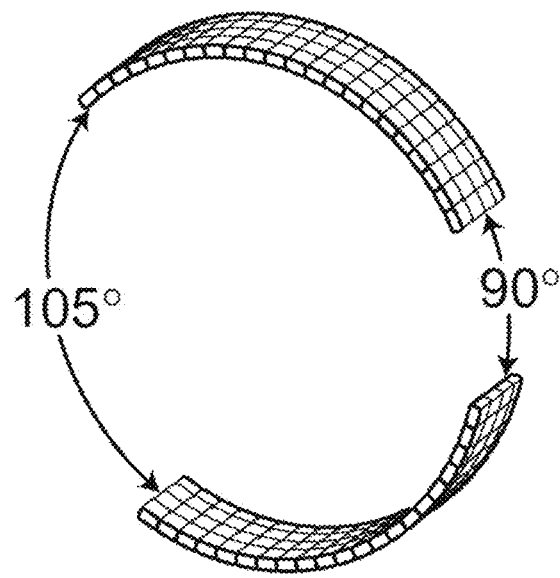
Figure 5C:
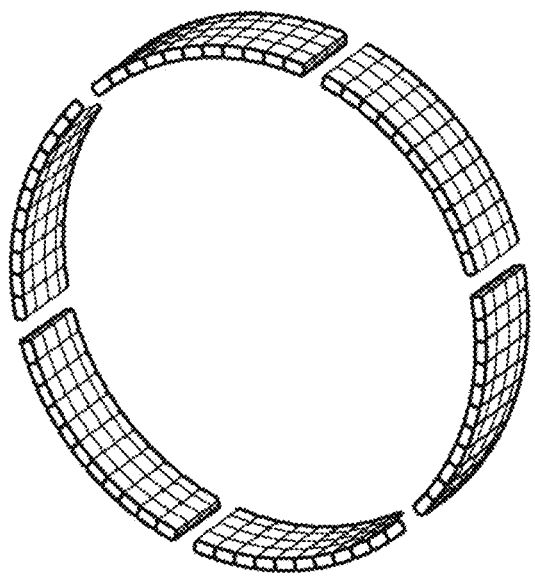
Figure 5D:
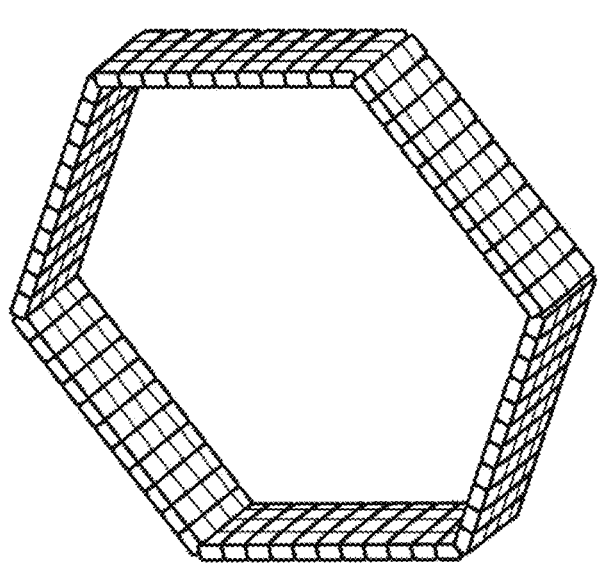

FIGS. 5A-5D are schematic diagrams illustrating exemplary detector rings according to some embodiments of the present disclosure. In some embodiments, a plurality of detector cassettes (or detector blocks) may be arranged in an array of full or partial rings. A detector ring may include one or more rings of detector blocks. For example, as illustrated in FIGS. 5A-5D, a detector ring may include four rings of detector blocks. A detector ring may have a diameter of 70 centimeters to 100 centimeters. In some embodiments, a detector ring with the full ring configuration may be configured in a circular form (see FIG. 5A), hexagonal form (see FIG. 5D), elliptic form, or another polygon form. In some embodiments, a detector ring with a partial ring configuration may be realized based on two or more detector blocks. A detector block may be curved or flat. FIG. 5B illustrates a partial ring with a 15° angular shift between two curved detector blocks. FIG. 5C illustrates a partial ring with six uniformly spaced curved detector blocks. In some embodiments, with the partial ring geometry, the transverse FOV of the detector ring may be increased based on the same total crystal volume of the detector ring. In some embodiments, a plurality of detector rings may be configured successively in the axial direction to form a detector assembly with a large axial length (e.g., 0.75 meters to 2 meters). In a detector assembly, at least one of the detector rings may be have the full ring configuration, and/or at least one of the detector rings may be have the partial ring configuration. The detector assembly with a large axial length may have a large axial FOV (e.g., 0.75 m to 2 m). In some embodiments, the detector assembly with a large axial length may realize whole-body scanning.

Figure 6A:
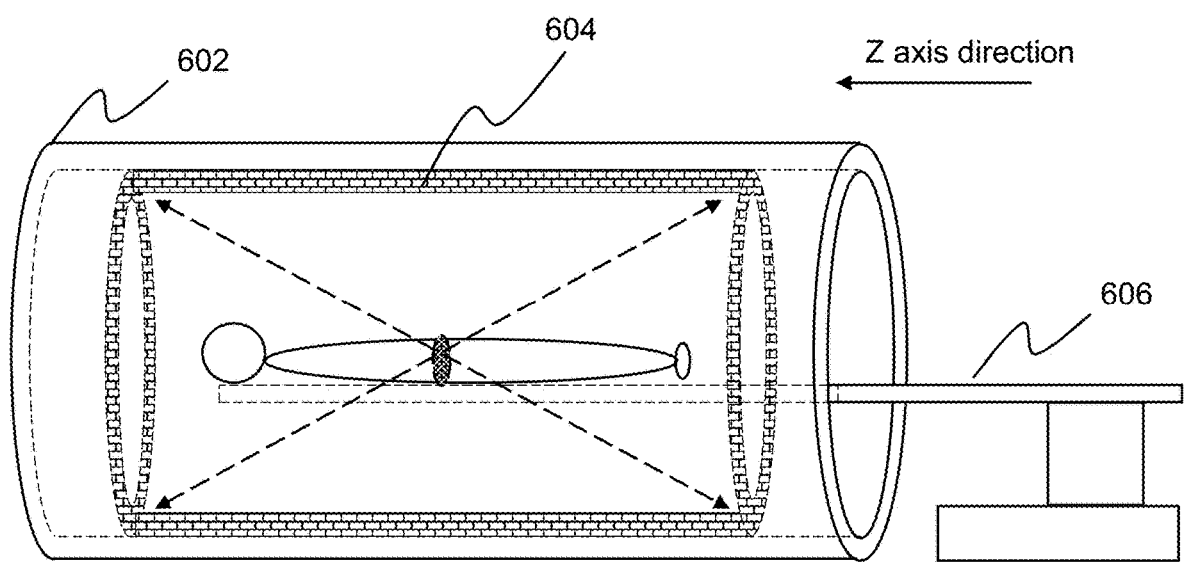
FIG. 6A is a schematic diagram illustrating an exemplary scanner according to some embodiments of the present disclosure.

FIG. 6A is a schematic diagram illustrating an exemplary scanner 110 according to some embodiments of the present disclosure. As shown in FIG. 6A, the scanner 110 may include a supporting assembly 602, a detector assembly 604, and a table 606. The supporting assembly 602 may be configured to support other components in the scanner 110 including, for example, the detector assembly 604, a cooling assembly (not shown in FIG. 6A), etc. For example, the supporting assembly 602 may be configured to support the detector assembly 604 and/or drive the detector assembly 604 to move, such as rotate, translate, swing, etc. In some embodiments, the supporting assembly 602 may include a bore (e.g., the detection region 113). The bore may have a first transverse diameter (or referred to as a bore transverse diameter) and a first axial length (or referred to as a bore axial length). The bore axial length may be defined as the distance from one end of the bore to an opposite end of the bore along a Z axis direction (i.e., the axial direction) indicated by the arrow as shown in FIG. 6A. The bore axial length may also refer to a length of the supporting assembly 602 along the Z axis direction. In some embodiments, the bore axial length of the supporting assembly 602 may be in a range from 0.75 meters to 2 meters. In some embodiments, the bore axial length of the supporting assembly 602 may exceed 2 meters.

Figure 6B:
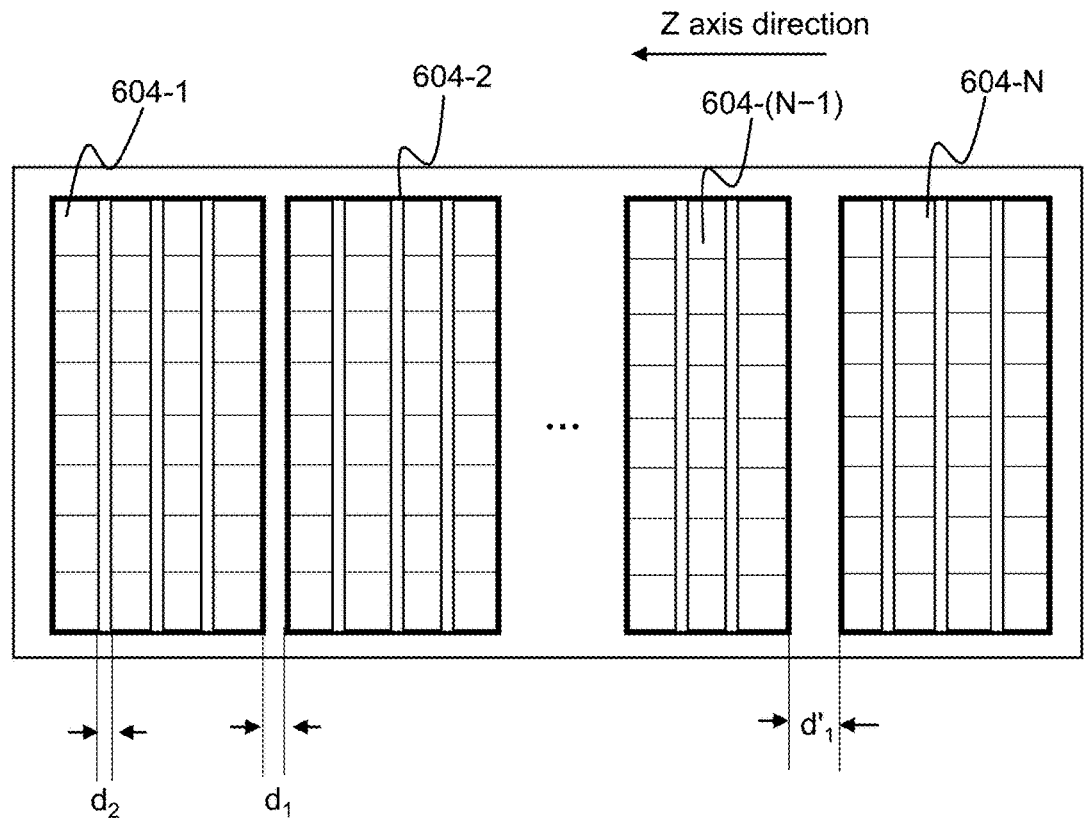
FIG. 6B is a schematic diagram illustrating an exemplary detector assembly of FIG. 6A illustrated in a two-dimensional plane according to some embodiments of the present disclosure.

The detector assembly 604 may include one or more detector modules (e.g., the detector modules 604-1, 604-2, . . . , 604-(N−1), 604-N as shown in FIG. 6B). A detector module may include one or more detector blocks. In some embodiments, the detector blocks may be arranged on an inner wall of the supporting assembly 602 in a certain number of rings. In some embodiments, the detector assembly 604 may have a second transverse diameter (or referred to as the transverse diameter of the detector assembly) and a second axial length (or referred to as the axial length of the detector assembly). The axial length of the detector assembly may be defined as a distance from one end of the detector assembly 604 to an opposite end of the detector assembly 604 along the Z axis direction. The axial length of the detector assembly may also refer to the length of the detector assembly 604 in the Z axis direction. The transverse diameter of the detector assembly may be defined as a diameter of a detector ring on the transverse plane perpendicular to the Z axis direction.

In some embodiments, the axial length of the detector assembly may relate to an axial field-of-view (AFOV) of the scanner 110. As used herein, the AFOV may refer to a maximum length along the Z axis direction of the detector assembly 604 to detect a coincidence event effectively (see FIG. 7B). The greater the axial length of the detector assembly 604 is, the larger the AFOV of the scanner 110 may be. For instance, the axial length of the detector assembly 604 may be in a range from 0.75 meters to 2 meters. In some embodiments, the axial length of the detector assembly 604 may exceed 0.75 meters, or 1 meter, or 1.5 meters, or 2 meters. Correspondingly, the axial length of the AFOV may exceed 0.75 meters, or 1 meter, or 1.5 meters, or 2 meters. Multiple organs (e.g., a head, a heart, a lung, a liver, a stomach, a pancreas, a bladder, a knee, etc.) of a subject may be scanned in a single scan. As another example, the axial length of the detector assembly 604 may be in a range from 0.75 meters to 1.25 meters. The region between the head and the thigh of a subject (e.g., an adult patient) may be scanned in a single scan, or a whole-body scan may be achieved in a single scan of a subject of a small size (e.g., a child). As a further example, the axial length of the detector assembly 604 may be in the range from 1.25 meters to 2 meters, or exceed 2 meters. In some embodiments, the bore axial length of the supporting assembly 602 may be equal to or greater than the axial length of the detector assembly 604.

The transverse diameter of the detector assembly 604 may relate to a transverse field-of-view (FOV) of the scanner 110. The transverse FOV may relate to an angle of acceptance for a scintillator of the detector assembly 604 to detect a coincidence event on the transverse plane (see FIG. 7A). The greater the transverse diameter of the detector assembly 604 is, the larger the transverse FOV of the scanner 110 may be. The transverse diameter of the detector assembly 604 may be smaller than the bore transverse diameter.

FIG. 6B is a schematic diagram illustrating an exemplary detector assembly 604 of FIG. 6A illustrated in a two-dimensional plane according to some embodiments of the present disclosure. As shown in FIG. 6B, the supporting assembly 602 may be an integrated structure. The detector assembly 604 may include one or more detector modules (e.g., the detector modules 604-1, 604-1, . . . , 604-(N−1), 604-N, etc.). Multiple detector modules may be mounted on the supporting assembly 602. Two adjacent detector modules may be spaced with a first gap (or referred to as a module gap) $d_1$ in the Z axis direction. In some embodiments, the first gap $d_1$ between two adjacent detector modules may be less than 20 millimeters (e.g., 1 millimeter, 2 millimeters, 5 millimeters, 10 millimeters, etc.). In some embodiments, the first gaps $d_1$ between any two adjacent detector modules in the detector assembly 604 may be equal to or less than 20 millimeters, or 15 millimeters, or 10 millimeters, or 8 millimeters, or 5 millimeters, or 3 millimeters, or 2 millimeters, or 1 millimeter. In some embodiments, the first gap $d_1$ may be less than a width of a scintillator in the Z axis direction. In some embodiments, the first gap $d_1$ between different detector modules may be the same or different. For example, two adjacent detector modules (e.g., a first detector module and a second detector module) may be spaced by 1 millimeters, while two adjacent detector modules (e.g., a third detector module and a fourth detector module) may be spaced by 5 millimeters. As another example, the detector modules in the detector assembly 604 may be spaced uniformly in the Z axis direction.

A detector module may include one or more detector blocks (or detector units, detector cassettes) as described in connection with FIGS. 4A, 4B, and/or 4C. The detector blocks (or detector units, detector cassettes) may be configured as one or more detector rings (e.g., detector rings with a full ring configuration and/or detector rings with a partial ring configuration) of a detector module. In a detector module, two adjacent detector rings may be spaced with a second gap (or referred to as a ring gap) $d_2$ in the Z axis direction. In some embodiments, the second gap $d_2$ may be less than 1 mm (e.g., 0.1 mm, 0.2 mm, 0.5 mm, etc.). In some embodiments, the second gap $d_2$ between two adjacent detector rings may be less than 5 millimeters. In some embodiments, the second gap $d_2$ between two adjacent detector rings may be less than 2 millimeters. In some embodiments, the gap $d_1$ of two adjacent detector modules may be the same as or different from the gap $d_2$ of two adjacent detector rings.

In some embodiments, the number of detector blocks (or detector units, detector cassettes) in different detector modules may be the same or different. For example, the detector module 604-1 and the detector module 604-2 may include the same number of detector blocks. As another example, the detector module 604-(N−1) and the detector module 604-N may have different numbers of detector blocks. In some embodiments, the sizes of detector blocks (or detector units, detector cassettes) in different detector modules may be the same or different. In some embodiments, the sizes of detector blocks (or detector units, detector cassettes) in the same detector module may be the same or different. In some embodiments, the transverse diameters of detector rings in different detector modules may be the same or different. In some embodiments, the transverse diameters of detector rings in the same detector module may be the same or different.

Figure 6C:
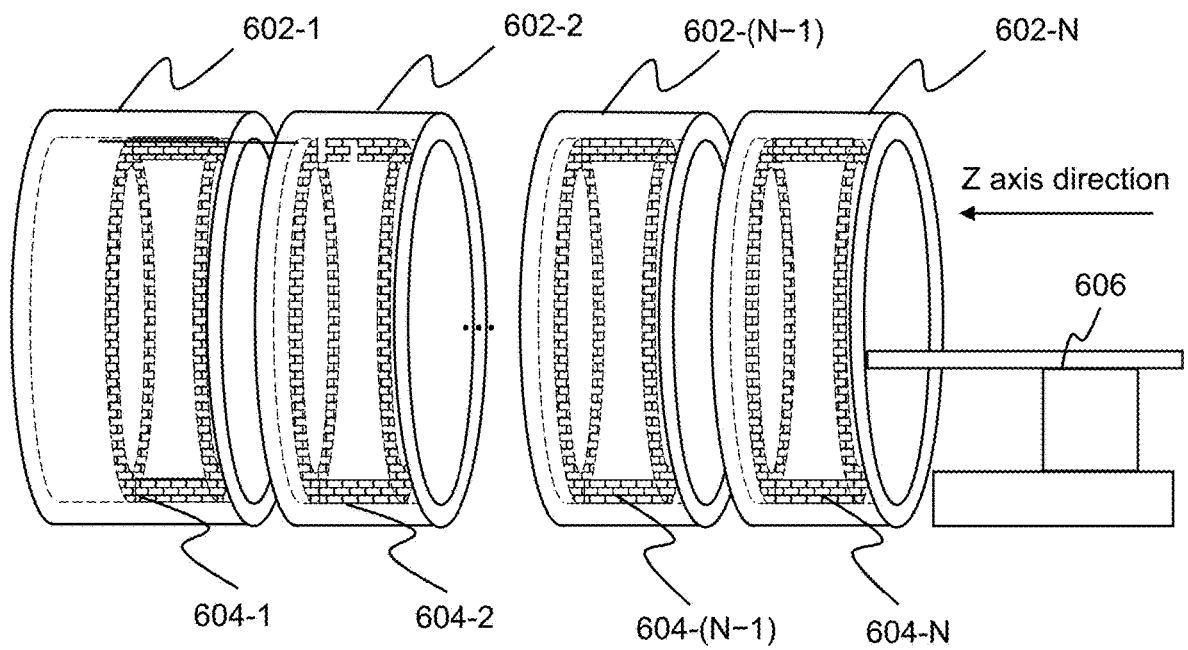
FIG. 6C is a schematic diagram illustrating another exemplary scanner according to some embodiments of the present disclosure.

FIG. 6C is a schematic diagram illustrating another exemplary scanner 110 according to some embodiments of the present disclosure. As shown in FIG. 6C, the scanner 110 may include a supporting assembly 602, a detector assembly 604, and a table 606. In some embodiments, the supporting assembly 602 may not be an integrated structure. The supporting assembly 602 may include one or more supporting modules, for example, a supporting module 602-1, a supporting module 602-2, . . . , a supporting module 602-(N−1), a supporting module 602-N, etc. The detector assembly 604 may include one or more detector modules, for example, a detector module 604-1, a detector module 604-2, . . . , a detector module 604-(N−1), a detector module 604-N, etc., as described in FIG. 6A. As shown in FIG. 6C, the multiple detector modules may be mounted on the multiple supporting modules, respectively. For example, the detector module 604-1 may be mounted on the supporting module 602-1, the detector module 604-2 may be mounted on the supporting module 602-2, the detector module 604-(N−1) may be mounted on the supporting module 602-(N−1), and the detector module 604-N may be mounted on the supporting module 602-N. In some embodiments, two adjacent supporting modules may be connected to each other by way of, such as, for example, welding, riveting, bolting, etc. In some embodiments, a detector module may be assembled on a supporting module to configure an imaging unit (e.g., a PET unit). In some embodiments, different imaging units may be used to scan different portions of a subject. In some embodiments, the length of an axial FOV of an imaging unit may range from 0.16 meters to 0.3 meters. In some embodiments, the length of an axial FOV of an imaging unit may range from 0.1 meters to 0.5 meters. In some embodiments, the length of an axial FOV of an imaging unit may be equal to or larger than a width of a detector block in the axial direction. In some embodiments, one or more imaging units may be assembled in the scanner 110 along the Z axis direction to obtain a large AFOV (e.g., 0.75 meters to 2 meters) for whole-body scanning (see, FIG. 6E). In some embodiments, the axial length of the AFOV may exceed 0.75 meters, or 1 meter, or 1.5 meters, or 2 meters.

In some embodiments, each imaging unit may have a center (e.g., a center in the transverse plane). In some embodiments, a deviation of the center of a first imaging unit (e.g., the imaging unit assembled based on the supporting module 602-1 and the detector module 604-1) and the center of a second imaging unit (i.e., an imaging unit other than the first imaging unit, e.g., the imaging unit assembled based on the supporting module 602-N and the detector module 604-N) may be below or equal to x millimeters. In some embodiments, x may be less than 1 millimeter. In some embodiments, x may range from 0.2 millimeters to 1 millimeter. In some embodiments, x may be less than 0.2 millimeters. In some embodiments, a deviation of the center of a first imaging unit and the center of a second imaging unit that is located adjacent to the first imaging unit is below or equal to 1 millimeter, or 0.5 millimeters, or 0.2 millimeters. In some embodiments, one or more imaging units may be adjusted in the transverse plane, so that the transverse plane of the imaging unit(s) may be substantially parallel to the transverse plane of the scanner 110.

Figure 6D:
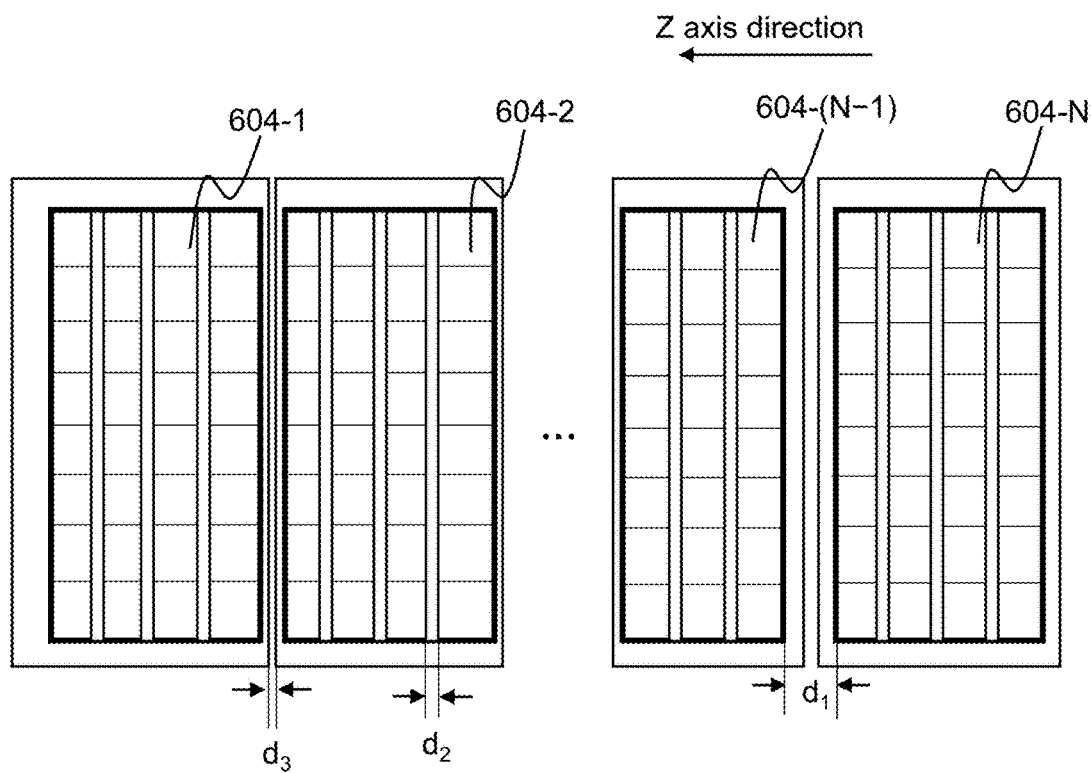
FIG. 6D is a schematic diagram illustrating an exemplary detector assembly of FIG. 6C illustrated in a two-dimensional plane according to some embodiments of the present disclosure.

FIG. 6D is a schematic diagram illustrating an exemplary detector assembly 604 of FIG. 6C illustrated in a two-dimensional plane according to some embodiments of the present disclosure. As illustrated in FIG. 6D, two adjacent detector modules may be spaced by a first gap $d_1$. In some embodiments, the first gap $d_1$ may be less than a width of a scintillator in the Z axis direction. The second gap $d_2$ between adjacent detector rings may be similar to that described in FIG. 6B. Two adjacent supporting modules may be spaced by a third gap $d_3$. In some embodiments, the third gap $d_3$ may be less than the first gap $d_1$. In some embodiments, the third gap $d_3$ between two adjacent supporting modules may be less than 20 millimeters. In some embodiments, the third gap $d_3$ between two adjacent supporting modules may be less than 5 millimeters. In some embodiments, the third gap $d_3$ between two adjacent supporting modules may be less than 2 millimeters. In some embodiments, the first gap $d_1$, the second gap $d_2$, and/or the third gap $d_3$ may be the same or different. For example, the first gap $d_1$ and the second gap $d_2$ may be equal. As another example, the third gap $d_3$ may be greater than the second gap $d_2$.

Figure 6E:
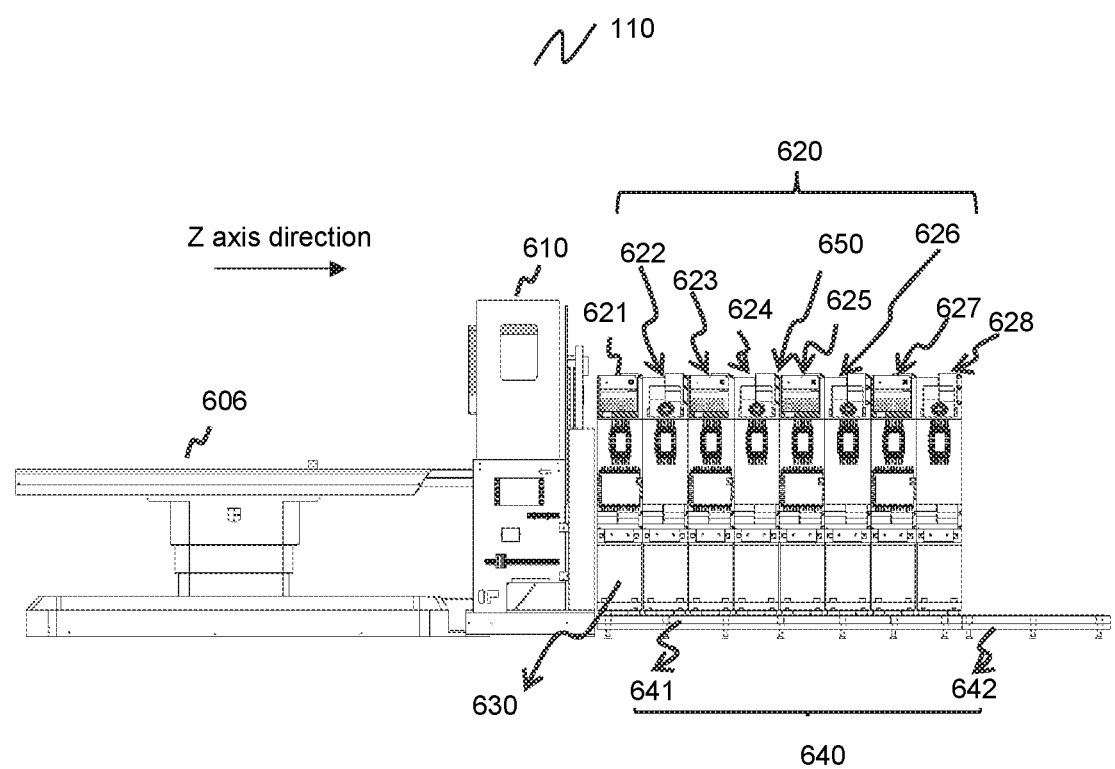
FIG. 6E is a schematic diagram illustrating an exemplary multi-modal scanner according to some embodiments of the present disclosure.

FIG. 6E is a schematic diagram illustrating an exemplary multi-modal scanner 110 according to some embodiments of the present disclosure. As shown in FIG. 6E, the multi-modal scanner 110 may include a first scanner 610, a PET scanner 620, a position adjustment assembly 630, a rail 640, and a detection region (not shown).

In some embodiments, the first scanner 610 may include a computed tomography (CT) scanner, an X-rays scanner, an MRI scanner, or the like, or a combination thereof. The first scanner 610 may be positioned at the front of the PET scanner 620 in the Z axis direction. In some embodiments, the first scanner 610 may include an X ray emission device and a first detector assembly. The first detector assembly may form a first portion of the detection region. The first detector assembly may be configured to detect at least a portion of an X ray beam emitted by the X ray emission device and traversing the subject located within the first portion of the detection region.

The PET scanner 620 may include one or more PET units (e.g., a PET unit 621, a PET unit 622, a PET unit 623, a PET unit 624, a PET unit 625, a PET unit 626, a PET unit 627, a PET unit 628, etc.). In some embodiments, a PET unit may include a detector module (e.g., the detector modules 604-1, 604-2, . . . , 604-N as shown in FIGS. 6C and 6D) and a supporting module (e.g., the supporting modules 602-1, 602-2, . . . , 602-N as shown in FIGS. 6C and 6D). In some embodiments, one or more detector modules of the PET scanner 620 may form a second portion of the detection region. Two adjacent PET units may be connected by way of, for example, bolting, riveting, screwing, welding, or the like, or a combination thereof. In some embodiments, the two adjacent PET units may be spaced with a gap 650 ranging from 1 millimeter to 20 millimeters. In some embodiments, the gap 650 between two adjacent PET units may be in a range from 2 millimeters to 10 millimeters. In some embodiments, the gap 650 between two adjacent PET units may be in a range from 2 millimeters to 5 millimeters. In some embodiments, the gap 650 may be less than a width of a scintillator in the Z axis direction. In some embodiments, the length of an axial FOV of a PET unit may range from 0.16 meters to 0.3 meters. In some embodiments, the length of an axial FOV of a PET unit may range from 0.1 meters to 0.5 meters. In some embodiments, the length of an axial FOV of an imaging unit may be equal to or larger than a width of a detector block in the axial direction.

The position adjustment assembly 630 may be configured to adjust the positions of the PET scanner 620 (e.g., the multiple PET units) and/or the first scanner 610 for alignment in the Z axis direction and/or in the transverse plane. In some embodiments, the position adjustment assembly 630 may include one or more position adjustment modules. A position adjustment module may be associated with one of the multiple PET units. The position adjustment module may be configured to move a PET unit associated with the position adjustment module.

In some embodiments, each PET unit may have a center (e.g., a center in the transverse plane). In some embodiments, a deviation of the center of a first PET unit (e.g., the PET unit 621) and the center of a second imaging unit (i.e., a PET unit other than the first PET unit, e.g., the PET unit 622, the PET unit 623, the PET unit 624, the PET unit 625, the PET unit 626, the PET unit 627, the PET unit 628, etc.) may be below or equal to y millimeters. In some embodiments, y may be less than 1 millimeter. In some embodiments, y may range from 0.2 millimeters to 1 millimeter. In some embodiments, y may be less than 0.2 millimeters. In some embodiments, a deviation of the center of a first PET unit (e.g., the PET unit 621) and the center of a second PET unit (e.g., the PET unit 622) that is located adjacent to the first PET unit is below or equal to 1 millimeter, or 0.5 millimeters, or 0.2 millimeters. In some embodiments, the deviation of the center of different PET units may be adjusted by the position adjustment assembly 630. In some embodiments, the deviation of the centers of the first scanner 610 and the PET scanner 620 may be adjusted by another position adjustment assembly (not shown). In some embodiments, one or more PET units may be adjusted in the transverse plane, so that the transverse plane of the PET unit(s) may be substantially parallel to the transverse plane of the multi-modal scanner 110. In some embodiments, the first scanner 610 and/or the PET scanner 620 may be adjusted in the transverse plane, so that the transverse plane of the first scanner 610 and/or the PET scanner 620 may be substantially parallel to the transverse plane of the multi-modal scanner 110.

The rail 640 may include a support rail 641 and a service rail 642. In some embodiments, the support rail 641 may be configured to support the position adjustment assembly 630. The supporting rail 641 may guide the PET unit(s) to be assembled or detached. In some embodiments, the support rail 641 may include one or more slides. The position adjustment assembly 630 may move along the multiple slides. In some embodiments, one or more of the PET units may be detachable. A PET unit may be assembled to or detached from the PET scanner 620 through the slide(s). The service rail 642 may be configured to support the multi-modal scanner 110. In some embodiments, the service rail 642 may include multiple wheels. The multi-modal scanner 110 may move with the wheels. In some embodiments, the service rail 642 may be detachable with the multi-modal scanner 110. More descriptions of the multi-modal scanner 110 may be found in U.S. patent application Ser. No. 15/609,251 entitled "SYSTEM AND METHOD FOR MEDICAL IMAGING," filed May 31, 2017, and Chinese Patent Application No. 201710075120.1 entitled "PET IMAGING DEVICE AND PET-CT IMAGING DEVICE." filed Feb. 13, 2017, the contents of which are hereby incorporated by reference.

As illustrated in FIGS. 6A-6E, a PET scanner with large AFOV (e.g., 0.75 meters to 2 meters) may facilitate whole-body scanning. Thus, a low-dose scan, a fast scan, a whole-body dynamic scan may be achieved. For a scan using a traditional PET scanner, the injection dose of fluorodeoxy-glucose may be 10 mci, a corresponding radiation dosage may be 7 mSv. A PET scanner with large AFOV (e.g., 0.75 meters to 2 meters), the radiation dose for a scan may be less than 1 mSv, about one tenth of a current level. The PET scanner with a large AFOV (e.g., 0.75 meters to 2 meters) may be used in a physical examination, the scanning of a child, etc. For a PET-CT scanner, the radiation dose for whole-body CT scanning may be in a range from 2 mSv to 15 mSv (120 kV, 20-150 mAs/slice). The radiation dose for CT scanning may be reduced by way of dose modulation, iterative reconstruction, using PET topogram instead of CT topogram, etc.

In some embodiments, the sensitivity of the PET scanner with a large AFOV (e.g., 0.75 meters to 2 meters) may be no less than 400 cps/kBq. In some embodiments, the sensitivity of the PET scanner with a large AFOV (e.g., 0.75 meters to 2 meters) may be higher than 350 cps/kBq, 300 cps/kBq, 250 cps/kBq, 200 cps/kBq, etc. In some embodiments, the scanning time for a scan may be less than 30 seconds. In some embodiments, the scanning time for a whole-body scan may be within 8 seconds to 20 seconds. A single-breath hold may be enough for whole-body scan. In some embodiments, a fast scan may reduce motion artifact. In some embodiments, the spatial resolution of the PET scanner with a large AFOV (e.g., 0.75 meters to 2 meters) may be higher than or equal to 5 millimeters, or 4 millimeters, or 3 millimeters, or 2 millimeters, or 1 millimeter. For instance, the spatial resolution of the PET scanner with a large AFOV (e.g., 0.75 meters to 2 meters) may be 2.8 millimeters, or 2.5 millimeters, or 2 millimeters, or higher than 2 millimeters. In some embodiments, the spatial resolution of the PET scanner with a large AFOV (e.g., 0.75 meters to 2 meters) may be higher than or equal to 2.8 millimeters. It should be noted that a spatial resolution of a relatively small value may be higher than a spatial resolution of a relatively large value. For instance, a spatial resolution of 2.5 millimeters may be higher than a spatial resolution of 2.8 millimeters.

It should be noted that the above description of the diagrams in FIGS. 6A-6E is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the scanner 110 in FIGS. 6A-6D may further include one or more components, such as one or more electronics modules. As another example, the number of PET units in FIG. 6E may be any integer larger than 0 (e.g., 8). As still another example, the number of imaging units in FIGS. 6C and 6D may be any integer larger than 0 (e.g., 8, or a number between 2 and 20, or a number between 4 and 8, etc.).

Figure 7A:
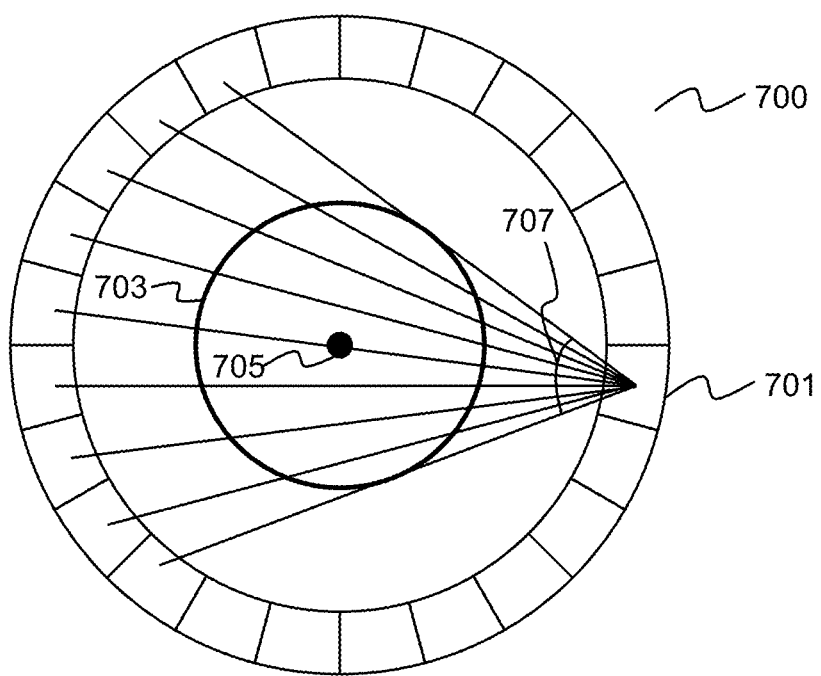
FIG. 7A is a schematic diagram illustrating an exemplary transverse FOV according to some embodiments of the present disclosure.

FIG. 7A is a schematic diagram illustrating an exemplary transverse FOV according to some embodiments of the present disclosure. In some embodiments, a detector unit (e.g., the detector unit 701) of a detector ring 700 may be connected by a coincidence circuit (not shown) of the electronics module 115 with a time window to a plurality of opposing detector units in the transverse plane. In some embodiments, the time window may be set at 1 nanosecond to 20 nanoseconds depending on the type of detector. In some embodiments, the detector ring 700 may have P detector units. In some embodiments, the detector unit 701 may be in coincidence with Q detector units on the opposite side. In some embodiments, Q may be a fraction of P, for example, Q=P/3, Q=P2, Q=2P/3, etc. Therefore, Q projections may be available for the detector unit 701. The Q projections for the detector unit 701 may form an angle of acceptance in the transverse plane. In some embodiments, similar to the detector unit 701, each detector unit may form an angle of acceptance in the transverse plane, and the angles of acceptance for all detector units in the detector ring 700 may form the transverse field of view (FOV). In some embodiments, the transverse FOV may be an overlapping region formed by the projections for all detector units in the detector ring 700. The larger the number of detector units in multicoincidence with each detector unit, the larger the angle of acceptance and hence the larger transverse FOV for the imaging system 100. In some embodiments, the transverse FOV may be determined based on a user input, or a default setting of the imaging system 100. In some embodiments, the transverse FOV may be determined based on performance of the imaging system 100, for example, a sensitivity, a spatial resolution, a time resolution, a response time, etc. In some embodiments, the transverse FOV may be determined based on the configuration of the detector ring 700, for example, the size of a detector unit, the thickness of a detector unit, the diameter of the detector ring 700, the gap between two adjacent detector units of the detector ring 700, etc. In some embodiments, the transverse FOV may relate to the diameter of the detector ring 700 and/or the transverse angle of acceptance. In some embodiments, the transverse FOV may have a diameter ranging from 60 centimeters to 90 centimeters.

Figure 7B:
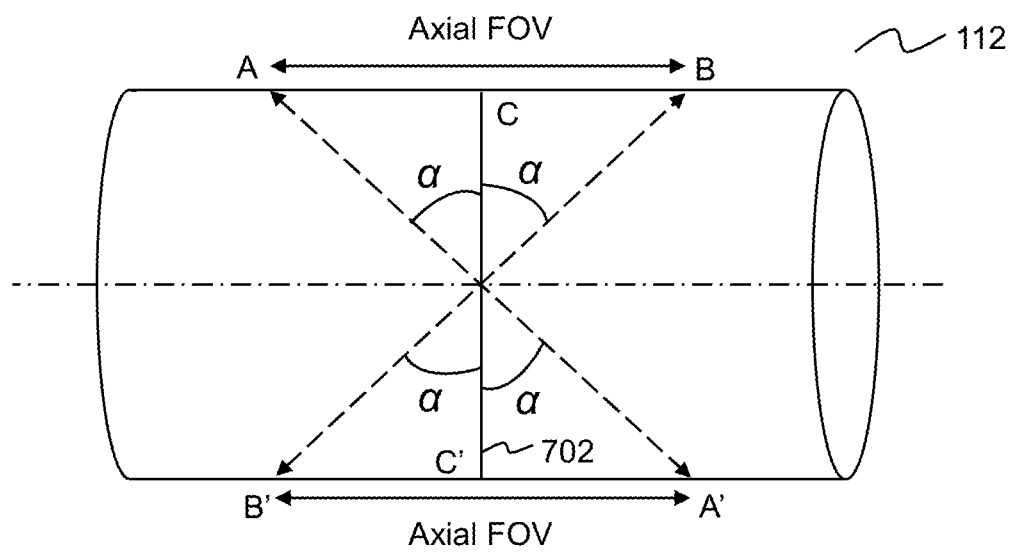
FIG. 7B is a schematic diagram illustrating an exemplary axial FOV according to some embodiments of the present disclosure.

FIG. 7B is a schematic diagram illustrating an exemplary axial FOV according to some embodiments of the present disclosure. In some embodiments, a detector unit (e.g., the detector unit A) of the detector assembly 112 may be connected by a coincidence circuit (not shown) of the electronics module 115 with a time window to a plurality of opposite detector units in the axial plane. In some embodiments, the time window may be set at 1 nanosecond to 20 nanoseconds depending on the type of detector. In some embodiments, the detector assembly 112 may have E rings of detector units. In some embodiments, the detector unit A may be in coincidence with F detector units in the axial direction on the opposite side. In some embodiments, F may be a fraction of E, for example, F=E/3, F=E/2, F=2E/3, F=E, etc. Therefore, F projections may be available for the detector unit A. Each of the F projections may form an angle relative to the transverse plane 702. The maximum angle (e.g., α) for the F projections may constitute the axial angle of acceptance. The detector unit A and the detector unit B (or, the detector unit A' and the detector unit B') may be positioned on opposite sides of the transverse plane 702. Both the detector unit A and the detector unit B (or, the detector unit A' and the detector unit B') may form the axial angle of acceptance. Then, the distance between the detector unit A and the detector unit B (or, the detector unit A' and the detector unit B') may form the axial FOV. In some embodiments, the axial FOV may be determined based on a user input, or a default setting of the imaging system 100. In some embodiments, the axial FOV may be determined based on the performance of the imaging system 100, for example, a sensitivity, a spatial resolution, a time resolution, a response time, etc. In some embodiments, the axial FOV may be determined based on the configuration of the detector assembly 112, for example, the size of a detector unit, the axial thickness of a detector ring, the diameter of the detector ring, the interval between two adjacent detector rings, the axial length of the detector assembly 112, etc. In some embodiments, the axial FOV may be less than 0.75 meters. In some embodiments, the axial FOV may be larger than 0.75 meters, for example, from 0.75 meters to 2 meters, etc. In some embodiments, for a large axial FOV (e.g., 0.75 meters to 2 meters), the time window of the coincidence circuit may be relatively large (e.g., 10 nanoseconds, 20 nanoseconds, 25 nanoseconds, etc.). In some embodiments, for a large axial FOV (e.g., 0.75 meters to 2 meters), different detector units may have different time windows. For example, detector units (e.g., the detector unit A and the detector unit B') far from the transverse plane 702 may have a time window of 20 nanoseconds, while detector units (e.g., the detector unit C and the detector unit C') close to the transverse plane 702 may have a time window of 1 nanosecond.

Figure 7C:
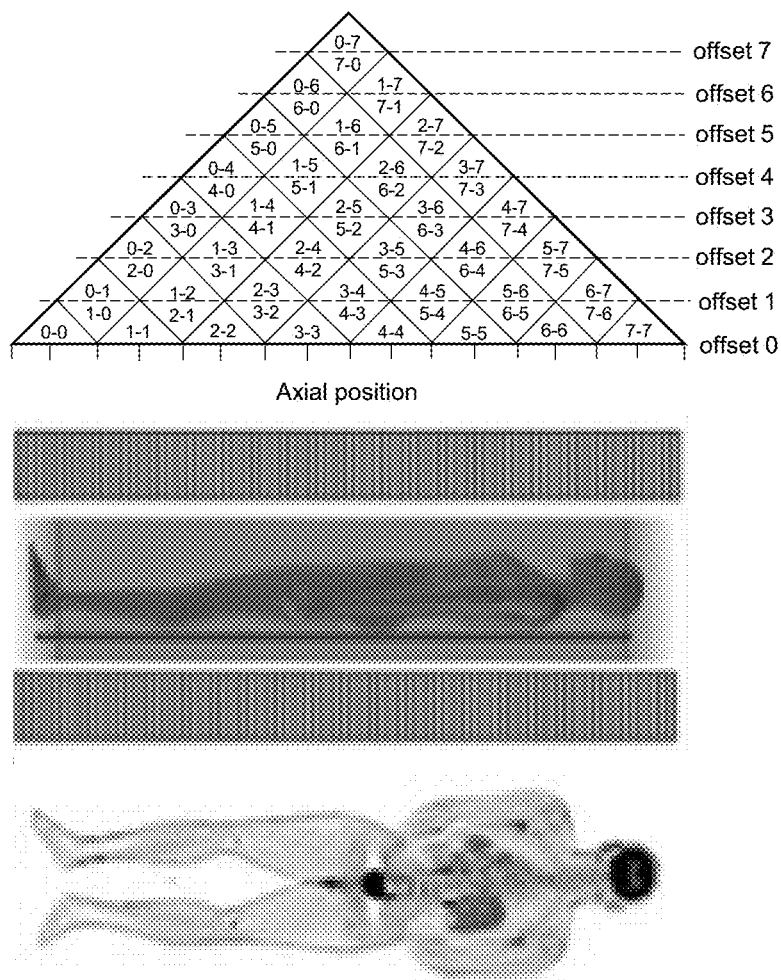
FIG. 7C is a schematic diagram illustrating a relationship between an exemplary detector assembly and the sensitivity of the imaging system according to some embodiments of the present disclosure.

FIG. 7C is a schematic diagram illustrating a relationship between an exemplary detector assembly 112 and the sensitivity of the imaging system 100 according to some embodiments of the present disclosure. As shown in FIG. 7C, the imaging system 100 may include eight PET units (e.g., the PET unit 621, the PET unit 622, the PET unit 623, the PET unit 624, the PET unit 625, the PET unit 626, the PET unit 627, the PET unit 628 as illustrated in FIG. 6E). In some embodiments, the length of the axial FOV of each of the eight PET units may be 0.25 meters. It should be noted that the number of the axial FOV of each of the eight PET units is merely provided for the purposes of illustration, and not intended to limit the scope of the present disclosure. The triangle regions (e.g., 0-0, 1-1, 2-2, 3-3, 4-4, 5-5, 6-6, and 7-7) may refer to sensitivities relating to coincidence events detected by one of the PET units. For example, the triangle region 0-0 may refer to sensitivities relating to coincidence events detected by the PET unit 621. The diamond regions (e.g., 0-1, 1-2, 2-3, 3-4, 4-5, 5-6, 6-7, etc.) may indicate different sensitivities relating to cross coincidence events detected by different PET units (e.g., two adjacent PET units). For example, the diamond region 0-1 (also 1-0) may refer to sensitivities relating to cross coincidence events detected by the PET unit 621 and the PET unit 622. The lines of response (LOR) between the PET units may be set by a user via the terminal(s) 130. As used herein, the line of response (LOR) may refer to a line between two scintillators that may detect a coincidence event. The inclination angle of a coincidence line may relate to a sensitivity of the imaging system 100. The greater the inclination angle of a coincidence line is, the higher the sensitivity of the imaging system 100 may be. In some embodiments, the inclination angle of a line of response may be defined by an offset of the line of response. In some embodiments, if coincidence events detected by two adjacent PET units need to be processed, the offset of the line of response may be equal to 0, and the sensitivity of the imaging system 100 may relate to the accumulation of sensitivities in the triangle regions (e.g., 0-0, 1-1, 2-2, 3-3, 4-4, 5-5, 6-6, and 7-7). The greater the offset is, the higher the sensitivity of the imaging system 100 may be.

Figure 8A:
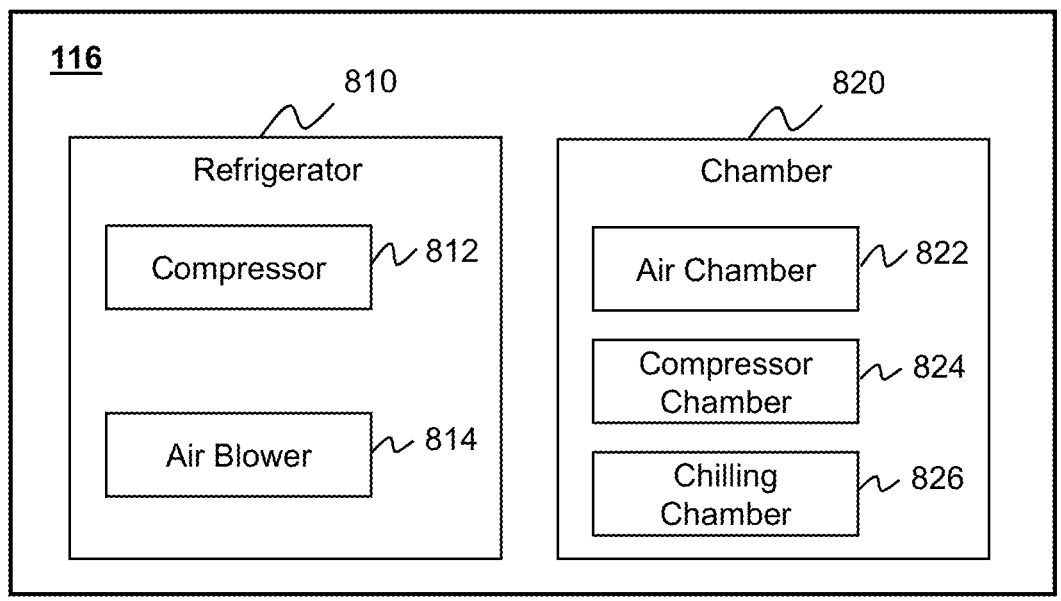
FIG. 8A is a schematic diagram illustrating an exemplary cooling assembly according to some embodiments of the present disclosure.

FIG. 8A is a schematic diagram illustrating an exemplary cooling assembly 116 according to some embodiments of the present disclosure. The cooling assembly 116 may use a cooling medium that is gas, liquid, or the like, or a combination thereof. For illustration purposes and not intended to limit the scope of the present disclosure, the cooling assembly 116 of FIG. 8A and FIG. 8B uses a gaseous cooling medium, or referred to as a cooling gas for brevity. The cooling assembly 116 may produce, transfer, deliver, channel, or circulate cooling gas to the scanner 110 to absorb heat produced by the scanner 110 during an imaging procedure. In some embodiments, the cooling assembly 116 may be entirely integrated into the scanner 110 and become a part of the scanner 110. In some embodiments, the cooling assembly 116 may be partially integrated into the scanner 110 and associated with the scanner 110. For example, a portion of the cooling assembly 116 (e.g., the chamber 820) may be integrated into the scanner 110, while another portion of the cooling assembly 116 (e.g., the refrigerator 810) may be configured outside the scanner 110. The cooling assembly 116 may allow the scanner 110 to maintain a suitable and/or stable working temperature. In some embodiments, the cooling assembly 116 may control the temperature at one or more target locations of the scanner 110. The target location may include the detector assembly 112, the electronics module 115, and/or any other component that may generate heat. As illustrated in FIG. 8A, the cooling assembly 116 may include a refrigerator 810 and a chamber 820.

The refrigerator 810 may process or cool down the cooling medium. The cooling medium may be introduced into the chamber 820 to absorb heat from the scanner 110 (e.g., the detector assembly 112). Exemplary gaseous cooling medium may include an inert gas, nitrogen, carbon dioxide, air, or the like, or a combination thereof. In some embodiments, the refrigerator 810 may cool heated cooling medium that has absorbed heat from the scanner 110.

As illustrated, the refrigerator 810 may include a compressor 812 and an air blower 814. The compressor 812 may increase the pressure of a coolant, then, the coolant may be condensed, and the heat in the coolant may be dissipated through a heat sink. In some embodiments, the condensed coolant may be evaporated by an evaporator (not shown), and absorb heat in the cooling gas, and then the heated cooling gas may be cooled down for reuse. The cooling gas may be driven by the air blower 814 and flow in the cooling assembly 116 cyclically. In some embodiments, the compressor 812 may include a centrifugal compressor, an axial compressor, a reciprocating compressor, a rotary compressor, or the like, or a combination thereof. For example, the axial compressor may include a diagonal or mixed-flow compressor, an axial-flow compressor, etc. The reciprocating compressor may include a diagram compressor, a double acting compressor, a single acting compressor, etc. The rotary compressor may include a rotary vane compressor, a scroll compressor, a rotary screw compressor, an ionic liquid piston compressor, a lobe compressor, a liquid ring compressor, etc. The air blower 814 (also referred to as fan) may drive the cooling gas to flow in the chamber 820. In some embodiments, the air blower 814 may include a mechanical bearing blower, a magnetic suspension blower, a gas suspension bearing blower, etc. In some embodiments, one or more parameters relating to a cooling process, such as a flow rate of the cooling gas, may be determined and/or adjusted by the air blower 814. For example, the flow rate of the cooling gas may be regulated through the variation of the rotation speed of the air blower 814.

The chamber 820 may be configured to channel the cooling gas to one or more target locations (e.g., around the detector assembly 112) of the scanner 110. As illustrated in FIG. 8A, the chamber 820 may include one or more air chambers 822, a compressor chamber 824, and one or more chilling chambers 826. The compressor chamber 824 may be configured to receive the cooling gas processed by the compressor 812. In some embodiments, the compressor chamber 824 may house the compressor 812. In some embodiments, the compressor chamber 824 may be connected to the compressor 812 via, for example, a pipe. The chilling chamber(s) 826 may be located around the heating components (e.g., the detector assembly 112, the electronics module 115 of the scanner 110, etc.) to cool the heating components.

The air chamber 822 may provide a location for gas communication between the compressor chamber 824 and one or more chilling chambers 826. For example, the air chamber 822 may include one or more inlet chambers connecting the compressor chamber 824 and the chilling chamber(s) 826. The cooling gas exiting the compressor 812 may be driven by the air blower 814 to flow from the compressor chamber 824 to the chilling chamber(s) 826 through the inlet chambers. As another example, the air chamber 822 may include one or more outlet chambers connecting the compressor chamber 824 and the chilling chamber(s) 826. The gas absorbing heat from the heating components (e.g., the detector assembly 112, the electronics module 115 of the scanner 110, etc.) may be driven to flow from the chilling chamber(s) 826 to the compressor chamber 824 though the outlet chambers.

In some embodiments, the configuration between the detector assembly 112 and the chilling chamber(s) 826 may be various. For example, one detector module of the detector assembly 112 may be configured to have one chilling chamber 826. As another example, multiple detector modules (e.g., all detector modules) of the detector assembly 112 may be configured to share one chilling chamber 826. In some embodiments, a first number of detector modules may be configured to share one single chilling chamber 826. The first number may be higher than 2 but lower than the number of the detector modules in the detector assembly 112.

In some embodiments, the configuration between the air chamber 822 and the chilling chamber 826 may be various. For example, one of the chilling chambers 826 may be configured to have one air chamber 822. As another example, multiple (e.g., all) chilling chambers 826 may be configured to share one air chamber 822. In some embodiments, a second number of chilling chambers 826 may be configured to share one single air chamber 822. The second number may be higher than 2 but lower than the number of the chilling chambers 826.

Figure 8B:
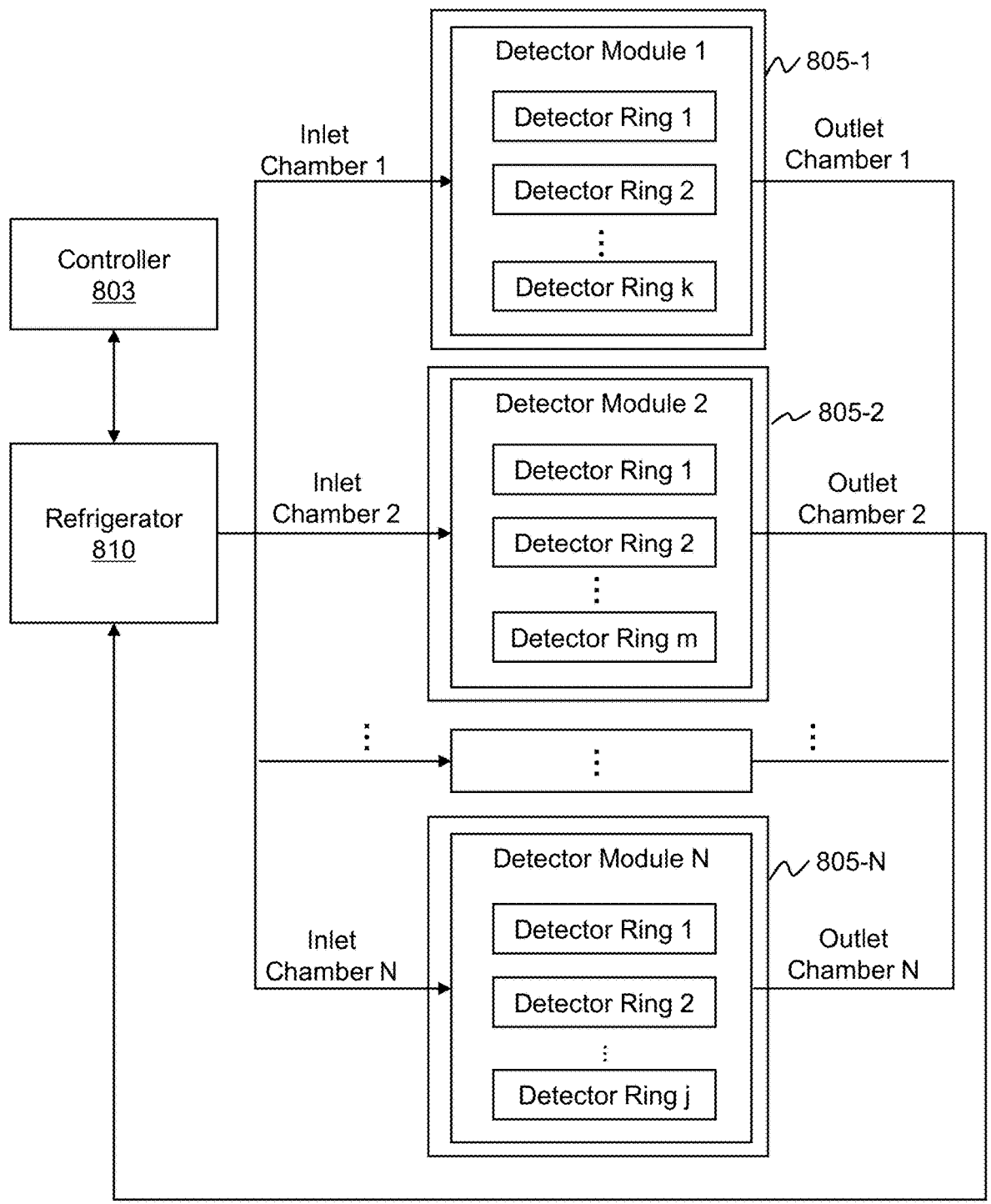
FIG. 8B is a schematic diagram illustrating an exemplary air cooling assembly and multiple detector modules according to some embodiments of the present disclosure.

FIG. 8B is a schematic diagram illustrating an exemplary air cooling assembly and multiple detector modules according to some embodiments of the present disclosure.

The refrigerator 810 may provide cooling gas as described in connection with FIG. 8A. The controller 803 may control the refrigerator 810, the chilling chambers 805, inlet chambers, and/or outlet chambers. In some embodiments, the controller 803 may be integrated in the control module 1004. In some embodiments, the controller 803 may control a parameter of the cooling gas in the refrigerator 810, the chilling chambers 805, inlet chambers, and/or outlet chambers respectively according to for example, an instruction set by a user via the terminal 130. The parameter of the cooling gas may include a pressure, a temperature, a flow rate of the cooling gas, a rate of heat generation, a cooling load to remove the generated heat, a cooling rate, or the like, or a combination thereof. For example, the controller 803 may adjust a pressure of the cooling gas (e.g., a gas pressure) in an inlet chamber (e.g., inlet chamber 1, inlet chamber 2, . . . , inlet chamber N). As another example, the controller 803 may control a flow rate of the cooling gas in one of the multiple inlet chambers and/or the outlet chambers respectively. Furthermore, the parameter of the cooling gas (e.g., the pressure, the temperature, the flow rate, etc.) in the inlet chambers (e.g., inlet chamber 1, inlet chamber 2, . . . , inlet chamber N) and/or the outlet chambers (e.g., outlet chamber 1, outlet chamber 2, . . . , outlet chamber N) may be different or the same.

In some embodiments, one of the multiple inlet chambers may be connected to one of the chilling chambers 805. One of the chilling chambers 805 may be configured with one of the detector modules (e.g., a detector module 1, a detector module 2, . . . , a detector module N). A detector module may include one or more detector rings. For example, the detector module 805-1 may include k detector rings. As another example, the detector module 805-2 may include m detector rings. As still another example, the detector module 805-N may include j detector rings. One of the multiple outlet chambers may be connected to one of the chilling chambers 805. The cooling gas provided by the refrigerator 810 may bypass the multiple inlet chambers and flow to the multiple chilling chambers 805, respectively. The numbers k, m, j and N are integers larger than 0. The numbers k, m, j and N may be the same or different.

In some embodiments, the flow rate of the cooling gas delivered to a detector module may be controlled based on the rate heat is generated in that detector module. For instance, if the temperature of a detector module increases beyond a threshold, or the temperature of a detector module increases at a rate beyond a threshold, the flow rate of the cooling gas delivered to that detector module may be increased. In some embodiments, the delivery of the cooling gas to various heating components may be controlled individually. For instance, the flow rates of the cooling gas to various detector modules may be different. The flow rate of the cooling gas to a heating component may be changed by changing the opening of one or more valves (not shown) configured in the chilling chamber 805 and/or the inlet chamber.

It should be noted that the above description of the air cooling assembly in FIGS. 8A and 8B is merely provided for the purposes of illustration, and not intended to limit the scope of the present disclosure. For persons having ordinary skills in the art, multiple variations or modifications may be made under the teachings of the present disclosure. For example, the cooling assembly 116 may further include one or more components, such as one or more thermal insulation layers. As another example, the cooling assembly 116 may further include one or more chambers configured as the cooling gas passage. As still another example, the detector module 1 and the detector module 2 may be configured with one chilling chamber, also referred to that the chilling chamber 805-1 and the chilling chamber 805-2 may be integrated into one chilling chamber. As a further example, the chilling chamber 805-1 and the chilling chamber 805-2 may communicate with each other. In some embodiments, the chilling chamber 805-1 and the chilling chamber 805-2 may be configured with one inlet chamber and/or one outlet chamber. However, those variations and modifications do not depart from the scope of the present disclosure. More descriptions of the air cooling assembly may be found in U.S. patent application Ser. No. 15/175,785 entitled "SYSTEM AND METHOD FOR COOLING COMPONENTS IN AN IMAGING SYSTEM," filed Jun. 7, 2016, the contents of which are hereby incorporated by reference.

Figure 9A:
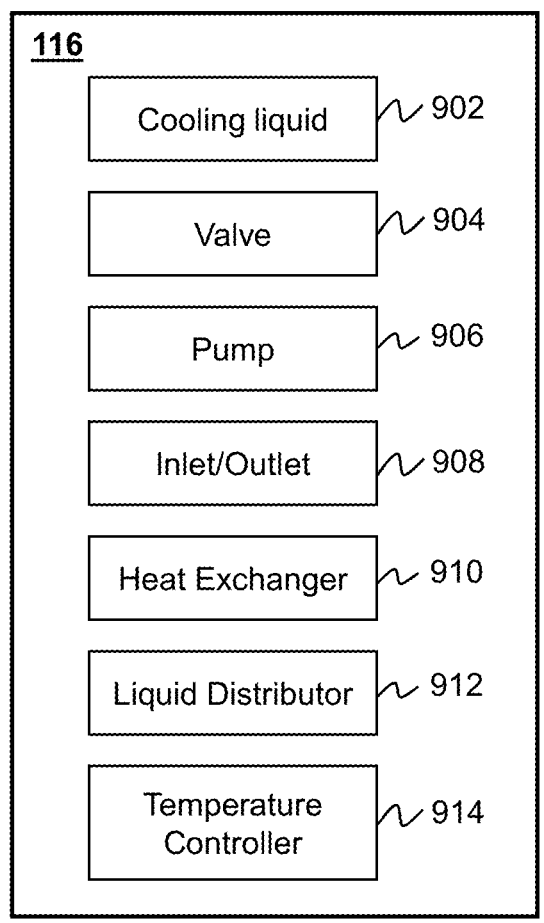
FIG. 9A is a schematic diagram illustrating another exemplary cooling assembly according to some embodiments of the present disclosure.

FIG. 9A is a schematic diagram illustrating another exemplary cooling assembly 116 according to some embodiments of the present disclosure. The cooling assembly 116 may use a cooling medium that is gas, liquid, or the like, or a combination thereof. For illustration purposes and not intended to limit the scope of the present disclosure, the cooling assembly 116 of FIG. 9A and FIG. 9B uses a liquid cooling medium, or a cooling liquid for brevity. As shown in FIG. 9A, the cooling assemble 116 may include a cooling liquid 902, a valve 904, a pump 906, an inlet/outlet 908, a heat exchanger 910, a liquid distributor 912, and a temperature controller 914. In some embodiments, the pump 906, the heat exchanger 910, and/or the liquid distributor 912 may be connected to each other via one or more pipes. In some embodiments, the temperature controller 914 may be connected to the valve 904, the pump 906, the inlet/outlet 908, the heat exchanger 910, and/or the liquid distributor 912 via a wireless connection and/or a wired connection.

The cooling liquid 902 may cool a heating component (e.g., the detector assembly 112, the electronics module 115 of the scanner 110, etc.) by absorbing and/or transferring the heat produced by the heating component. In some embodiments, the cooling liquid 902 may include water, oil, polyalkylene glycol (PAG), gutting fluid, nanofluid (e.g., CuO, alumina, titanium, carbon nanotubes, etc.), liquid gas (e.g., $CO_2$), freon, etc.

The valve 904 may be configured to control an on/off state of a pipe and/or a flow rate of the cooling liquid. In some embodiments, the valve 904 may be configured to control the flow velocity and/or the flow rate of the cooling liquid 902 from or to the pump 906, the heat exchanger 910, and/or the liquid distributor 912.

The pump 906 may drive the cooling liquid to flow in the liquid cooling assembly cyclically. In some embodiments, the pump 906 may include a positive displacement pump, an impulse pump, a velocity pump, a gravity pump, a steam pump, a valveless pump, a centrifugal pump, or the like, or a combination thereof. For example, the positive displacement pump may include a rotary lobe pump, a progressive cavity pump, a rotary gear pump, a piston pump, a diaphragm pump, a screw pump, a gear pump, a hydraulic pump, a rotary vane pump, a peristaltic pump, a rope pump, a flexible impeller pump, etc. In some embodiments, the pump 906 may be in fluid communication with the heat exchanger 910 via the inlet/outlet 908.

The inlet/outlet 908 may be connected to the heat exchanger 910. In some embodiments, the liquid cooling assembly may include an inlet and an outlet. In some embodiments, the pump 906, the heat exchanger 910, and/or the liquid distributor 912 may be configured to share the inlet/outlet 908. For example, the cooling liquid 902 may flow into or discharge from the pump 906, the heat exchanger 910, and/or the liquid distributor 912 through the inlet/outlet 908. In some embodiments, each of the pump 906, the heat exchanger 910, and/or the liquid distributor 912 may have its own inlet/outlet 908.

The heat exchanger 910 may be configured to transfer heat between the cooling liquid 902 and a refrigerant (also refer to as a coolant) including, for example, freon, an azeotropic mixture, a hydrocarbon refrigerant, or the like, or any combination thereof. For example, the cooling liquid 902 may absorb heat from a heating component (e.g., the detector assembly 112, the electronics module 115 of the scanner 110, etc.), and may flow to the heat exchanger 910 driven by the pump 906. The used cooling liquid 902 in the heat exchanger 910 may transfer the heat absorbed from the heating component to the refrigerant. In some embodiments, the refrigerant may be separated from the cooling liquid 902 by a solid wall to prevent the mixing of the two. In some embodiments, the heat exchanger 910 may include a shell and tube heat exchanger, a plate heat exchanger, a plate and shell heat exchanger, an adiabatic wheel heat exchanger, a plate fin heat exchanger, a pillow plate heat exchanger, a fluid heat exchanger, a waste heat recovery unit, a dynamic scraped surface heat exchanger, a phase-change heat exchanger, a direct contact heat exchanger, a microchannel heat exchanger, or the like, or a combination thereof.

The liquid distributor 912 may distribute the cooling liquid 902 to different channels. The channels may be configured to transfer the cooling liquid 902 to target locations (e.g., around the detector assembly 112, the electronics module 115 of the scanner 110, etc.). In some embodiments, the liquid distributor 912 may control an amount of the cooling liquid 902 distributed to one of the channels. For example, if a portion of the detector assembly 112 is at a high temperature, the liquid distributor 912 may increase the flow rate of the cooling liquid 902 to the channel corresponding to the portion of the detector assembly 112. As another example, the liquid distributor 912 may distribute the cooling liquid 902 to different channels equably. In some embodiments, the liquid distributor 910 may include various types including, for example, a pass type, a weir type, a pressure type liquid distributor, a spray type, a porous tube type, etc.

The temperature controller 914 may control a temperature of the heating component (e.g., the detector assembly 112, the electronics module 115 of the scanner 110, etc.) by controlling one or more modules in the water cooling assembly (e.g., the valve 904, the pump 906, the inlet/outlet 908, the heat exchanger 910, and/or the liquid distributor 912). For example, the temperature controller 914 may control the liquid distributor 910 to increase the flow rate of the cooling liquid 902 to one pipe corresponding to a detector assembly 112 to decrease the temperature of the detector assembly 112. As another example, the temperature controller 914 may control the pump 906 to increase a pressure and/or a flow velocity of the cooling liquid 902 to decrease the temperature of the heating component. As still another example, the temperature controller 914 may control the heat exchanger 910 to decrease the temperature of the cooling liquid 902 to decrease the temperature of the heating component. In some embodiments, the temperature controller 914 may include one or more temperature sensors connected with a target location (e.g., the detector assembly 112, the electronics module 115 of the scanner 110, etc.) to monitor the temperature relating to the target location.

Figure 9B:
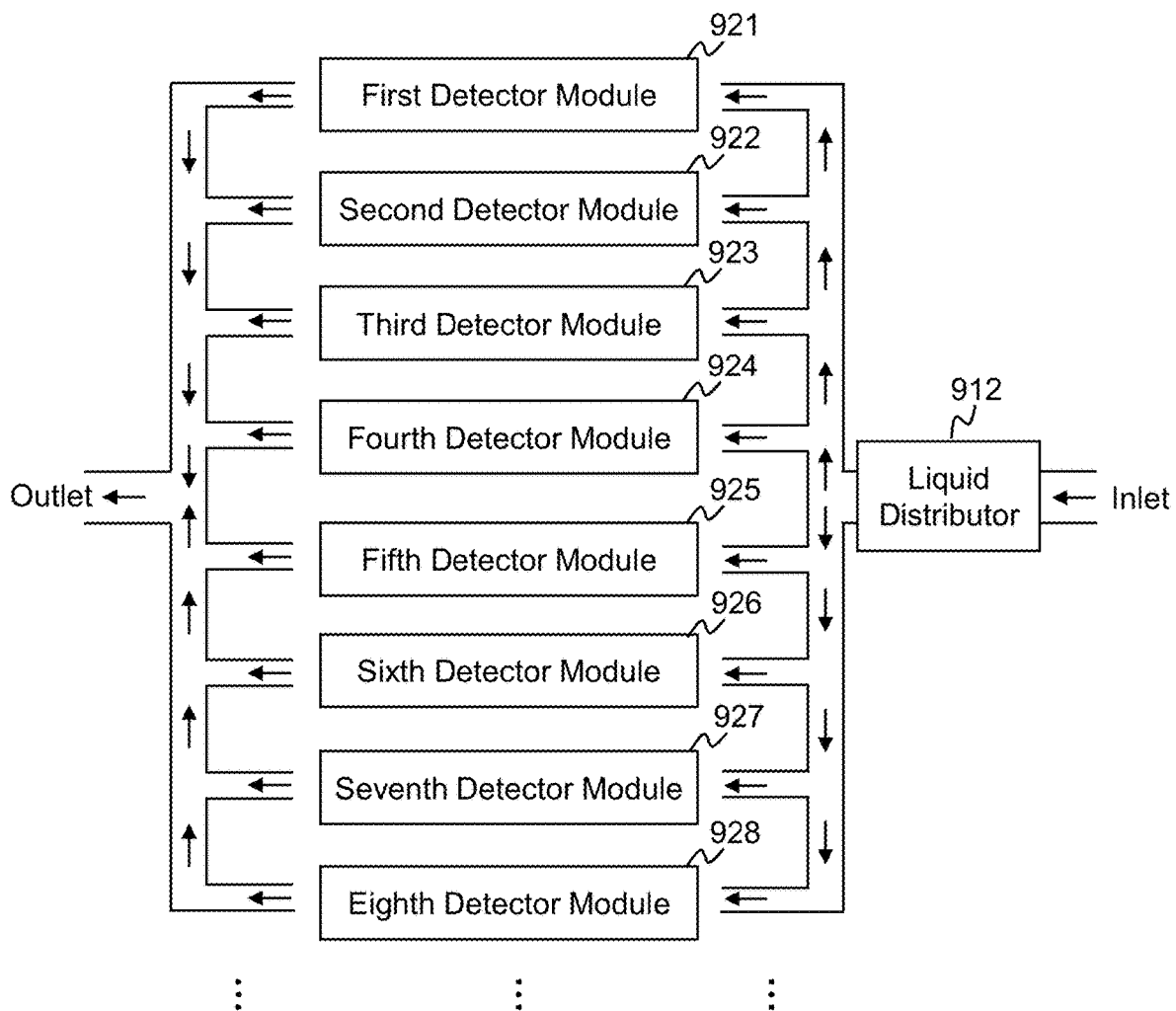
FIG. 9B is a schematic diagram illustrating an exemplary water cooling assembly and multiple detector modules according to some embodiments of the present disclosure.

FIG. 9B is a schematic diagram illustrating an exemplary water cooling assembly and multiple detector modules according to some embodiments of the present disclosure. As shown in FIG. 9B, the liquid distributor 912 may distribute the cooling liquid 902 into multiple pipes. The multiple pipes may be in fluid communication with different target locations around the multiple detector modules (e.g., a first detector module 921, a second detector module 922, a third detector module 923, a fourth detector module 924, a fifth detector module 925, a sixth detector module 926, a seventh detector module 927, an eighth detector module 928, etc.). One of the multiple pipes may be coupled to one detector module. In some embodiments, a pipe may cling to one or more surfaces of a detector module, and thus, the cooling liquid 902 flowing in the pipe may absorb heat from the detector module.

Figure 9C:
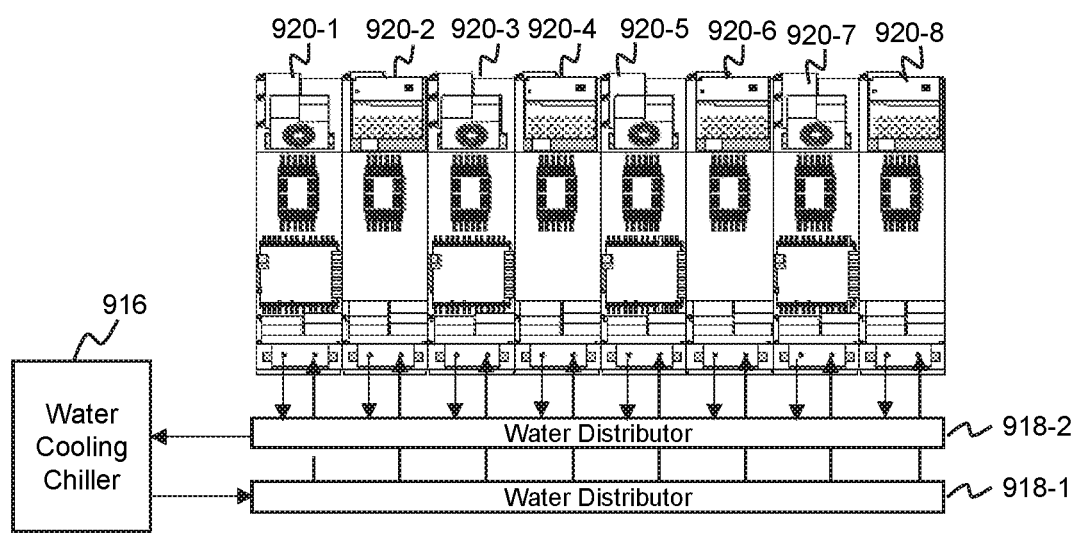
FIG. 9C is a schematic diagram illustrating another exemplary water cooling assembly and multiple detector modules according to some embodiments of the present disclosure.

FIG. 9C is a schematic diagram illustrating another exemplary water cooling assembly and multiple detector modules according to some embodiments of the present disclosure. As shown in FIG. 9C, the water cooling assembly may include a water cooling chiller 916 and at least two water distributors (e.g., a water distributor 918-1 and a water distributor 918-2). The water cooling chiller 916 may include a pump, an inlet/outlet, a heat exchanger, and/or a temperature controller 914 as described in connection with FIG. 9A. The water distributor 918-1 may be configured to distribute a cooling liquid (e.g., water) of a lower temperature, according to a specific flow rate, to multiple target regions around multiple detector modules. A detector module may include one or more detector rings. In some embodiments, a detector module may refer to a PET unit as illustrated in FIG. 6E. As shown in FIG. 9C, the water distributor 918-1 may distribute cooling liquid (e.g., water) to a first PET unit 920-1, a second PET unit 920-2, a third PET unit 920-3, a fourth PET unit 920-4, a fifth PET unit 920-5, a sixth PET unit 920-6, a seventh PET unit 920-7, an eighth PET unit 920-8, etc. It should be noted that the number of PET units is merely provided for the purposes of illustration, and not intended to limit the scope of the present disclosure. The water distributor 918-2 may be configured to converge the cooling liquid which have absorbed heat from the target regions around the multiple detector modules and transfer the heated liquid to the water cooling chiller 916.

In some embodiments, the water cooling chiller 916 may cool, within a period of time, a specific amount of cooling liquid to a lower temperature by a heat exchanger (e.g., the heat exchanger 910). A pump may drive the cooling liquid to flow to the water distributor 918-1 through an inlet. The water distributor 918-1 may distribute the specific amount of cooling liquid at the lower temperature into multiple portions and transfer the multiple portions of cooling liquid to multiple target regions around the multiple detector modules. The cooling liquid of the lower temperature may absorb heat generated by the detector modules or other heating components around the target regions (e.g., the electronics assembly 115). The used cooling liquid may be at a higher temperature after absorbing heat. Then the used cooling liquid of a higher temperature may be transferred to and mixed at the water distributor 918-2. The mixed used cooling liquid may be transferred back to the heat exchanger in the water cooling chiller 916. Then in the heat exchanger, the used cooling liquid at the higher temperature may be cooled to provide a cooled cooling liquid of a lower temperature for reuse. The water cooling assembly may perform the above operations cyclically to cool the scanner 110. More descriptions of the water cooling assembly in the scanner 110 may be found in Chinese Patent Application No. 201710075120.1 entitled "PET IMAGING DEVICE AND PET-CT IMAGING DEVICE," filed Feb. 13, 2017, the contents of which are hereby incorporated by reference.

It should be noted that the above description of the diagram in FIGS. 9A-9C is merely provided for the purposes of illustration, and not intended to limit the scope of the present disclosure. For persons having ordinary skills in the art, multiple variations or modifications may be made under the teachings of the present disclosure. For example, the valve 904 and/or the inlet/outlet 908 may be integrated into other modules in the cooling assembly 116, for example, the pump 906, the heat exchanger 910, and/or the liquid distributor 912. As another example, the cooling assembly 116 may include one or more pipes for transferring the cooling liquid 902 to one or more target locations. As still another example, one or more detector modules (e.g., PET unit) may be coupled to the same pipe. As a further example, the number of PET units may be any integer larger than 0. However, those variations and modifications do not depart the scope of the present disclosure.

Figure 10:
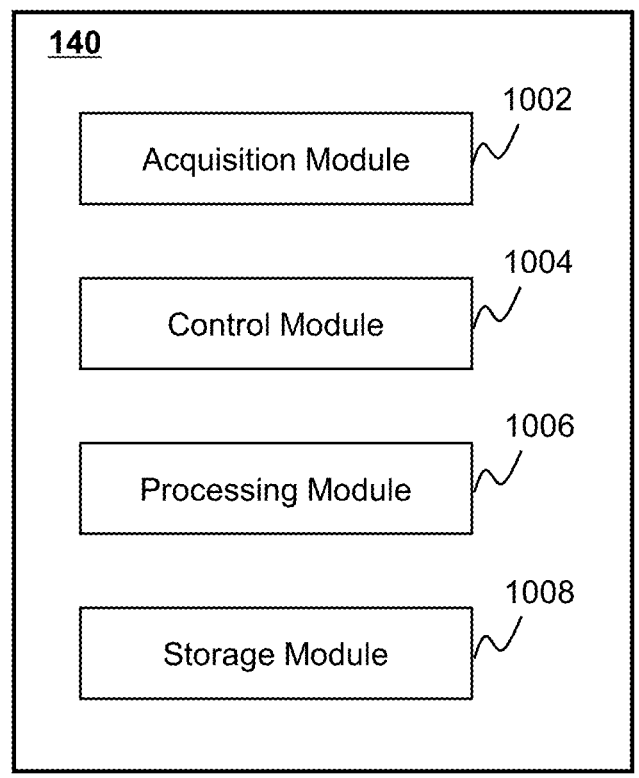
FIG. 10 is a schematic diagram illustrating an exemplary processing engine according to some embodiments of the present disclosure.

FIG. 10 is a schematic diagram illustrating an exemplary processing engine 140 according to some embodiments of the present disclosure. The processing engine 140 may include an acquisition module 1002, a control module 1004, a processing module 1006, a storage module 1008. At least a portion of the processing engine 140 may be implemented on a computing device.

The acquisition module 1002 may acquire data or signal. In some embodiments, the acquisition module 1002 may acquire the data from the scanner 110, the storage 150, the terminal(s) 130, and/or an external data source (not shown). In some embodiments, the data may include image data (e.g., projection data), instructions, or the like, or a combination thereof. For example, the image data may be generated based on the radiation rays (e.g., γ rays) that emit from a subject positioned in the detection region 113. In some embodiments, the image data may include information relating to energy of the radiation rays (e.g., γ rays), information relating to an interaction position of the radiation rays (e.g., γ rays) in the detector assembly 112, and/or information relating to an interaction time of the radiation rays (e.g., γ rays) in the detector assembly 112. The instructions may be executed by the processor(s) of the processing engine 140 to perform exemplary methods described in this disclosure. In some embodiments, the acquired data may be transmitted to the storage module 1008 for storing.

The control module 1004 may generate one or more control parameters for controlling the acquisition module 1002, the processing module 1006, the storage module 1008, the table 114, the detector assembly 112, the cooling assembly 116, the electronics module 115, or the like, or any combination thereof. For example, the control module 1004 may control the acquisition module 1002 as to whether to acquire image data. As another example, the control module 1004 may control the electronics module 115 as to whether to acquire an electrical signal, the time when an electrical signal acquisition may occur, or the frequency to acquire an electrical signal. As still another example, the control module 1004 may control the operation of the scanner 110 (e.g., the detector assembly 112, table 114, electronics module 115, cooling assembly 116, etc.). As a further example, the control module 1004 may control the processing module 1006 to select different algorithms to process the data acquired by the acquisition module 1002 or electrical signal acquired by the electronics module 115. In some embodiments, the control module 1004 may receive a real-time or a predetermined instruction provided by a user (e.g., a doctor, a technician, etc.) to control one or more operations of the scanner 110, the acquisition module 1002, and/or the processing module 1006. For example, the control module 1004 may adjust the acquisition module 1002 and/or the processing module 1006 to generate images of a subject according to the real-time or predetermined instruction. In some embodiments, the control module 1004 may communicate with other modules in the PET imaging system 100 for exchanging information and/or data.

The processing module 1006 may process information provided by various modules of the processing engine 140. The processing module 1006 may process data acquired by the acquisition module 1002, signal acquired by the electronics module 115, data retrieved from the storage module 1008, etc. In some embodiments, the processing module 1006 may reconstruct one or more images based on the data or signal according to a reconstruction technique, generate reports including the one or more images and/or other related information, and/or perform any other function for image reconstruction. The reconstruction technique may include an iterative reconstruction algorithm (e.g., a maximum likelihood expectation maximization (MLEM) algorithm, an ordered subset expectation maximization (OSEM) algorithm), a filtered back projection (FBP) algorithm, a 3D reconstruction algorithm, or the like, or any combination thereof. In some embodiments, the processing module 1006 may correct the data or reconstructed image based on one or more correction techniques. The correction technique may include a random correction, a scatter correction, an attenuation correction, a dead time correction, normalization, or the like, or any combination thereof. In some embodiments, the processing module 1006 may perform one or more corrections in image reconstruction.

The storage module 1008 may store data or signal, control parameter(s), processed data or signal, or the like, or a combination thereof. In some embodiments, the storage module 1008 may store one or more programs and/or instructions that may be executed by the processor(s) of the processing engine 140 to perform exemplary methods described in this disclosure. For example, the storage module 1008 may store program(s) and/or instruction(s) that may be executed by the processor(s) of the processing engine 140 to acquire data or signal, reconstruct an image based on the data or signal, and/or display any intermediate result or a resultant image.

In some embodiments, one or more modules illustrated in FIG. 10 may be implemented in at least part of the exemplary PET imaging system 100 as illustrated in FIG. 1. For example, the acquisition module 1002, the control module 1004, the storage module 1008, and/or the processing module 1006 may be integrated into a console (not shown). Via the console, a user may set the parameters for scanning a subject, acquiring data or signal, etc. In some embodiments, the console may be implemented via the processing engine 140 and/or an external device (not shown).

Figure 11:
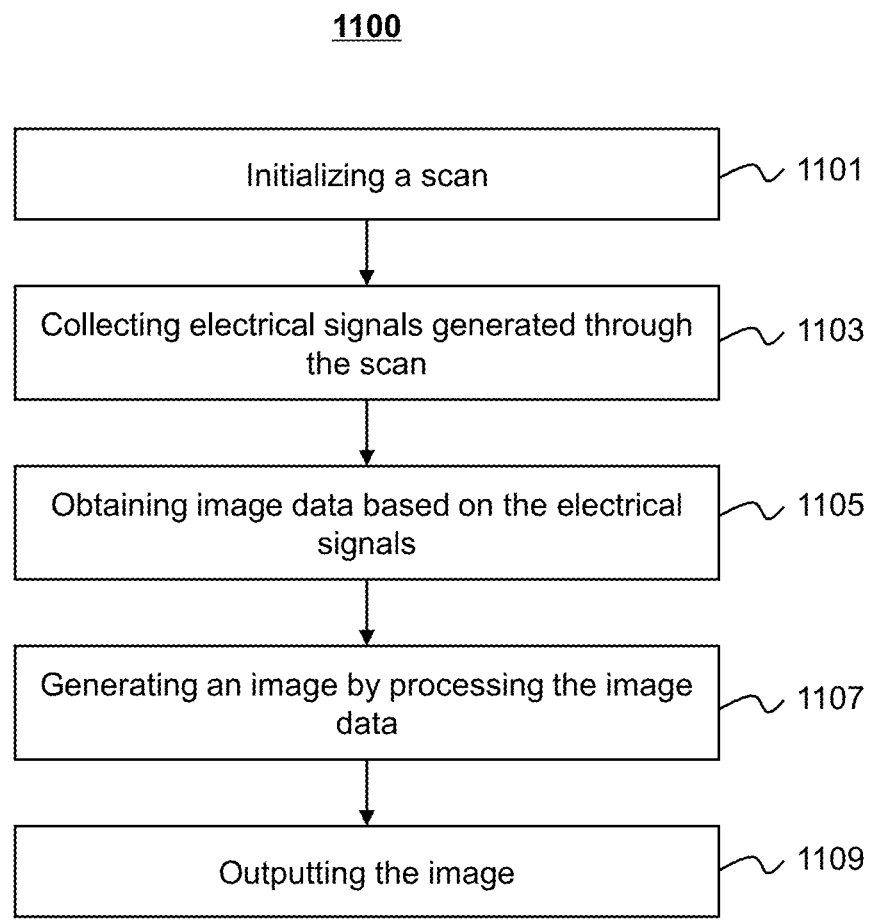
FIG. 11 is a flowchart illustrating an exemplary process for PET imaging according to some embodiments of the present disclosure.

FIG. 11 is a flowchart illustrating an exemplary process 1100 for PET imaging according to some embodiments of the present disclosure. In some embodiments, one or more operations of process 1100 illustrated in FIG. 11 for PET imaging may be implemented in the PET imaging system 100 illustrated in FIG. 1. For example, the process 1100 illustrated in FIG. 11 may be stored in the storage 150 in the form of instructions, and invoked and/or executed by the processing engine 140 (e.g., the processor of a computing device). As another example, a portion of the process 1100 may be implemented on the scanner 110.

In 1101, a scan may be initialized. In some embodiments, operation 1101 may be performed by the control module 1004. In some embodiments, the initialization may be performed based on a scanning protocol, a user input, a default setting of the imaging system 100, or the like, or any combination thereof. The scanning protocol may include a scan region of an object, a dose of a tracer isotope, an uptake period of the tracer isotope, or the like, or any combination thereof.

In some embodiments, the detector assembly 112 may be initialized in 1101. In some embodiments, the scanner 110 may have a large axial FOV (e.g., between 0.75 m and 2 m), and the detector assembly 112 may have an axial length larger than or equal to the axial FOV. As the number of detectors of the scanner 110 with a large axial FOV may be larger than that of a scanner with a normal axial FOV (e.g., from 0.16 meters to 0.3 meters, from 0.16 meters to 0.5 meters, etc.), the alignment and function of the detectors may be significant for achieving a good performance. In some embodiments, a validity test of the detector assembly 112 may be performed in 1101. For example, whether the detectors are aligned in the axial direction may be tested. As another example, whether the detectors in the axial FOV range are functional may be tested. With large axial FOV, more radiation rays may be detected, and the complexity for identifying which crystal has a radiation ray interaction may be increased. With more detectors, spatial distortions in crystal identification may be intensified. In some embodiments, positions of the detectors (or crystals) may be calibrated based on a position calibration algorithm, for example, a position calibration algorithm based on a crystal position look-up table. The crystal position look-up table may map the inaccurate interaction location to the exact interaction crystal position. The crystal position look-up table may be generated based on one or more algorithms including, for example, a principal component analysis (PCA)-based algorithm, a hierarchical fusion algorithm, a region segmentation based algorithm, or the like, or any combination thereof. In some embodiments, the crystal position look-up table may be generated or obtained in 1101. For example, the crystal position look-up table may be acquired from the storage 150, the storage module 1008, or an external data source (not shown). More descriptions regarding a crystal position look-up table may be found in, for example, U.S. Patent Publication No. US-2016-0321808-A1 entitled "METHOD AND SYSTEM FOR CRYSTAL IDENTIFICATION," published Nov. 3, 2016, the contents of which are incorporated by reference.

In some embodiments, the detector assembly 112 may be initialized to "enable" a portion of detectors while "disabling" the rest of detectors. For example, if the head of the object is to be scanned, a portion of detectors in a certain axial range (e.g., 20 centimeters) may be "enabled" to detect radiation rays emitted from the head, while the rest of detectors may not detect radiation rays even though there may be radiation rays reaching the rest of detectors. As another example, if the whole body of the object is to be scanned, a plurality of detectors surrounding the whole body (e.g., the detectors along the length of an axial FOV of 1.8 meters) may be selected to detect signals. In some embodiments, different detectors of the detector assembly 112 may be selected to detect signals at different times. The selection of detectors and the time to start scanning may be initialized in 1101 based on the scanning protocol. For example, a first portion of detectors may be "enabled" to scan the head at time $T_1$, while a second portion of detectors may be "enabled" to scan the feet at time $T_2$.

In some embodiments, the cooling assembly 116 may be initialized in 1101. In some embodiments, a flow rate (or a flux) of the cooling air or coolant may be initialized. In some embodiments, which air chamber (or which valve) is to be opened may be initialized. As the main function of the cooling assembly 116 may be cooling the detectors that generate heat, the cooling assembly 116 may be initialized based on the initialization of the detector assembly 112. For example, if a first portion of detectors are to be "enabled" to work at time $T_1$, the air chamber (or valve) that introduce the cooling air (or coolant) to the surface of the first portion of detectors may be opened at time $T_1$ or earlier than the time $T_1$, or the flow rate (or flux) of the cooling air or coolant that pass through the first portion of detectors may be increased at time $T_1$.

In some embodiments, one or more parameters may be initialized in 1101. The parameters may include scanning parameters, reconstruction parameters, etc. The scanning parameters may include a scan start time, a scan duration, a signal acquisition frequency, a coincidence time window, an offset (as illustrated in FIG. 7C), an energy threshold, etc. In some embodiments, the coincidence time window may relate to the offset. The larger the offset is, the larger the coincidence time window may be. In some embodiments, a variable coincidence time window may be set based on the offset. For example, a relatively small coincidence time window may be set if the offset is 0, while a relatively large coincidence time window may be set if the offset is larger than 0. The reconstruction parameters may include an image resolution, a filter, one or more parameters used in a reconstruction technique (e.g., an iteration time in iterative reconstruction, a coefficient, a threshold, etc.), or the like, or any combination thereof. In some embodiments, the parameters may be initialized based on a user input, a system default, or the like, or any combination thereof.

In some embodiments, a desired position of the table 114 may be initialized in 1101. The desired position may be in an FOV (e.g., the transverse FOV and the axial FOV) of the detection region 113. In some embodiments, the desired position of the table 114 may be initialized based on a scanning protocol, a user input, a system default, or the like, or any combination thereof. For example, the desired position of the table 114 may be determined based on a scan region of the subject. In some embodiments, the desired position of the table 114 may be associated with the "enabled" detectors. For example, the desired position of the table 114 may be within a special region surrounded by the "enabled" detectors. In some embodiments, the subject positioned on the table 114 may be moved to the desired position. The table 114 may be moved in the axial direction, a vertical position, and a horizontal direction perpendicular to the axial direction and the vertical position.

In 1103, electrical signals generated through the scan may be collected. In some embodiments, operation 1103 may be performed by the electronics module 115. A plurality of radiation rays may be received using the detector assembly 112. The radiation rays may be γ rays that emit from the subject positioned in the detection region 113. Before scanning, a radioactive tracer isotope may be injected into the subject. One or more atoms of the tracer isotope may be chemically incorporated into one or more biologically active molecules in the subject. The active molecules may become concentrated in one or more tissues of interest within the subject. The tracer isotope may undergo positron emission decay and emit one or more positrons. A positron may travel a short distance (e.g., about 1 mm) within a tissue of interest, lose kinetic energy and interact with an electron of the subject. The positron and the electron may annihilate and produce a pair of annihilation photons. The pair of annihilation photons (or radiation rays) may move in approximately opposite directions. A plurality of radiation rays may reach the detector assembly 112 and be received by the scintillators (e.g., the scintillator array 410) in the detector assembly 112. Then, the scintillators may absorb the energy of the radiation ray (e.g., γ ray) photons, and convert the absorbed energy into light. A plurality of electrical signals may be generated based on the absorbed radiation rays by the photosensors that couple to the scintillators.

In some embodiments, an interaction position and/or an interaction time of a received radiation ray may be determined by the electronics module 115. The interaction position may be used to identify which scintillator within the scintillators of the detector assembly 112 has a radiation ray interaction with the received radiation ray, and/or a depth of interaction of the received radiation ray in the identified scintillator. The interaction position may be determined based on the energy of the electrical signals and one or more algorithms including, for example, a centroid algorithm, the Anger-Logic algorithm, a maximum likelihood estimation algorithm, or a localization algorithm based on an artificial neutral network model, or the like, or any combination thereof. In some embodiments, the interaction time may be determined based on the energy and/or collection time of the electrical signals. In some embodiments, the interaction time may be determined based on a lower limit detection (LLD) circuit (or a constant fraction discriminator (CFD) circuit) and a time-to-digital converter (TDC). In some embodiments, the interaction time may be corrected based on the depth of interaction and a time correction technique. The time correction technique may include a dead time correction, a time walk correction, etc.

In 1105, image data may be obtained based on the electrical signals collected in 1103. In some embodiments, operation 1105 may be performed by the electronics module 115. In some embodiments, the image data may include data relating to one or more lines of response (LOR). In some embodiments, one or more coincidence events may be determined based on the interaction positions and the interaction times of a plurality of received radiation rays. If two radiation rays are received and interact with two scintillators within a certain time window (e.g., 1 nanosecond, 2 nanoseconds, 5 nanoseconds, 10 nanoseconds, 20 nanoseconds, etc.), the two radiation rays may be determined to come from the same annihilation, and regarded as a coincidence event. In some embodiments, the coincidence event may be determined by a coincidence circuit of the electronics module 115. The coincidence event may be assigned to a line of response (LOR) joining the two relevant scintillators that detect the coincidence event. The coincidence events that are assigned to the same line of response (LOR) may be projected and image data may be generated. In some embodiments, the image data may be stored as a sinogram in the storage 150, the storage module 1008, an external data source, etc. In some embodiments, the image data may be acquired by the acquisition module 1002 from the storage 150, the storage module 1008, an external data source, etc.

In 1107, an image may be generated based on the image data obtained in 1105. In some embodiments, operation 1107 may be performed by the processing module 1006. In some embodiments, the image data may be processed to generate an image. The image data may be processed based on one or more algorithms including, for example, denoising, a reconstruction algorithm, a correction algorithm, etc. In some embodiments, the reconstruction algorithm may include an iterative reconstruction algorithm (e.g., a maximum likelihood expectation maximization (MLEM) algorithm, an ordered subset expectation maximization (OSEM) algorithm), a filtered back projection (FBP) algorithm, a 3D reconstruction algorithm, or the like, or any combination thereof. In some embodiments, the correction algorithm may include a random correction, a scatter correction, an attenuation correction, a dead time correction, normalization, or the like, or any combination thereof. A reconstructed image may show a tracer distribution within the scanned subject. In some embodiments, a whole body image may be generated based on the electrical signals generated by a large axial FOV scanner (e.g., the scanner 110). In some embodiments, mechanical installation error (e.g., a deviation of the centers of two imaging units as described in FIG. 6C) may be corrected in image reconstruction.

In 1109, the image generated in 1107 may be outputted. In some embodiments, operation 1109 may be performed by the control module 1004. In some embodiments, the image may be outputted to the storage module 1008, the storage 150, an external data source, etc. for storing. In some embodiments, the image may be outputted to the terminal(s) 130 for displaying.

It should be noted that the above description of the process 1100 is merely provided for the purpose of illustration, and not intended to limit the scope of the present disclosure. For persons having ordinary skills in the art, multiple variations and modifications may be made to the process 1100 under the teachings of the present disclosure. However, those variations and modifications do not depart from the scope of the present disclosure. For example, an image segmentation operation may be added after operation 1107.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A system for imaging, comprising:
   a supporting assembly comprising a detection region to accommodate a subject; and
   a detector assembly surrounding the detection region, the detector assembly being configured to detect radiation rays emitted from the subject located within the detection region, the detector assembly including a plurality of detector rings, each detector ring comprising a scintillator array and a plurality of photosensors, the plurality of detector rings being arranged on the supporting assembly along an axial direction of the supporting assembly to form an axial field of view (FOV) having a length no less than 0.75 meters, wherein
      the detector assembly includes N detector modules, each of which comprises at least two of the plurality of detector rings,
      the supporting assembly includes N supporting modules, each of the N supporting modules being configured to support one of the N detector modules,
      the N detector modules and the N supporting modules are configured as N imaging units, each of which comprises at least one detector module of the N detector modules and at least one supporting module of the N supporting module, and at least one of the N imaging units is individually detachable from the system.

2. The system of claim 1, the supporting assembly further comprising a supporting rail along the axial direction to guide the N imaging units to be assembled.

3. The system of claim 1, further comprising a position adjustment assembly configured to align the N imaging units in the axial direction.

4. The system of claim 1, wherein each imaging unit of the N imaging units has a center, a deviation of the center of a first imaging unit and the center of a second imaging unit is less than or equal to 1 millimeter.

5. The system of claim 1, wherein N is between 4 and 8.

6. The system of claim 1, wherein two of the N imaging units have a first gap in the axial direction less than a width of one scintillator of the scintillator array in the axial direction.

7. The system of claim 6, wherein two supporting modules in the two adjacent imaging units of the N imaging units have a second gap in the axial direction, the second gap being less than 10 millimeters.

8. The system of claim 1, wherein the length of the axial FOV is larger than or equal to 1 meter.

9. The system of claim 1, having a spatial resolution higher than or equal to 2.8 millimeters.

10. The system of claim 1, having a sensitivity higher than or equal to 300 cps/kBq.

11. The system of claim 1, wherein the detection assembly detects radiation from the subject at a radiation dose less than or equal to 5 mSv in a scan of the subject using the system.

12. The system of claim 1, wherein at least two of the N imaging units are capable of operating at different times.

13. The system of claim 12, wherein the at least two of the N imaging units are capable of operating at different times according to at least one of a scanning protocol or a location of a subject to be scanned.

14. The system of claim 1, wherein a first imaging unit of the N imaging units has a first transverse diameter, a second imaging unit of the N imaging units has a second transverse diameter, and the first transverse diameter is different from the second transverse diameter.

15. A system for PET-CT imaging, comprising:
a supporting assembly comprising a detection region to accommodate a subject, the detection region including a first portion and a second portion;
an X ray emission device;
a first detector assembly surrounding the first portion of the detection region, the first detector assembly being configured to detect at least a portion of an X ray beam emitted by the X ray emission device and traversing the subject located within the first portion of the detection region;
a second detector assembly surrounding the second portion of the detection region, the second detector assembly being configured to detect radiation rays emitted from the subject located within the second portion of the detection region, the second detector assembly including a plurality of detector rings, each detector ring comprising a scintillator array and a plurality of photosensors, the plurality of detector rings being arranged on the supporting assembly in an axial direction of the supporting assembly to form an axial field of view (FOV) having a length no less than 0.75 meters, wherein
the second detector assembly includes N detector modules, each of which comprises at least two of the plurality of detector rings,
the supporting assembly includes N supporting modules, each of the N supporting modules being configured to support one of the N detector modules,
the N detector modules and the N supporting modules are configured as N PET units, each of which comprises at least one detector module of the N detector modules and at least one supporting module of the N supporting module, and
at least one of the N PET units is individually detachable from the system.

16. The system of claim 15, the supporting assembly further comprising a supporting rail along the axial direction to guide the N PET units to be assembled.

17. The system of claim 15, further comprising a position adjustment assembly configured to align the N PET units and the first detector assembly in the axial direction.

18. The system of claim 15, wherein each PET unit of the N PET units has a center, a deviation of the center of a first PET unit and the center of a second PET unit is less than or equal to 1 millimeter.

19. The system of claim 15, wherein two of the N PET units have a first gap in the axial direction less than a width of one scintillator of the scintillator array in the axial direction.

20. The system of claim 15, wherein the length of the axial FOV is larger than or equal to 1 meter.

* * * * *